US009072543B2

(12) United States Patent
Miller et al.

(10) Patent No.: US 9,072,543 B2
(45) Date of Patent: Jul. 7, 2015

(54) VASCULAR ACCESS KITS AND METHODS

(75) Inventors: Larry J. Miller, Spring Branch, TX (US); David S. Bolleter, San Antonio, TX (US); Robert W. Titkemeyer, San Antonio, TX (US); Charles M. Schwimmer, Los Gatos, CA (US)

(73) Assignee: VIDACARE LLC, Shavano Park, TX (US)

( * ) Notice: Subject to any disclaimer, the term of this patent is extended or adjusted under 35 U.S.C. 154(b) by 1309 days.

(21) Appl. No.: 11/380,340

(22) Filed: Apr. 26, 2006

(65) Prior Publication Data

US 2007/0084742 A1    Apr. 19, 2007

Related U.S. Application Data

(63) Continuation-in-part of application No. 10/449,503, filed on May 30, 2003, now Pat. No. 7,670,328.

(60) Provisional application No. 60/675,246, filed on Apr. 27, 2005, provisional application No. 60/384,756, filed on May 31, 2002.

(51) Int. Cl.
*A61B 19/02* (2006.01)
*A61B 17/34* (2006.01)
*A61M 5/158* (2006.01)

(52) U.S. Cl.
CPC ......... *A61B 17/3472* (2013.01); *A61B 19/0256* (2013.01); *A61B 19/0264* (2013.01);
(Continued)

(58) Field of Classification Search
CPC .......... A61B 17/3472; A61B 19/0264; A61M 2005/1581; A61M 2005/1585
USPC .............. 606/79–85, 176–182, 192; 604/154, 604/135, 136, 174, 180; 206/570, 571, 206/363–370
See application file for complete search history.

(56) References Cited

U.S. PATENT DOCUMENTS 2,317,648 A    4/1943    Skiveland ..................... 32/26
2,419,045 A    4/1947    Wittaker ..................... 128/305
(Continued)

FOREIGN PATENT DOCUMENTS

CA    2138842    6/1996
CA    2454600    2/2003
(Continued)

OTHER PUBLICATIONS

Liakat A. Parapia, Trepanning or trephines: a history of bone marrow biopsy, British Journal of Haematology, pp. 14-19, 2007.
(Continued)

*Primary Examiner* — Christopher Beccia
(74) *Attorney, Agent, or Firm* — Norton Rose Fulbright US LLP

(57) ABSTRACT

Kits carrying various components and devices are provided for use in obtaining access to a patient's vascular system. Various methods and procedures may be used to treat both emergency and more routine conditions using the contents of such kits. For example, such kits may contain various types of intraosseous (IO) devices including, but not limited to, drivers, penetrator assemblies, IO needles and other related components. Intravenous (IV) devices such as syringes, needles, IV bags, tubing and other related components for use in obtaining access to portions of a patient's vascular system may be included. Various types of connectors for communicating fluids with and/or monitoring a patient's vascular system may be provided. Such kits may contain medications, drugs and fluids used to treat a wide variety of both acute and chronic diseases and conditions.

14 Claims, 9 Drawing Sheets

(52) U.S. Cl.
CPC ......... *A61B2017/3492* (2013.01); *A61M 5/158* (2013.01); *A61M 2005/1581* (2013.01); *A61M 2005/1585* (2013.01); *A61M 2210/02* (2013.01)

(56) References Cited

U.S. PATENT DOCUMENTS

| | | | |
|---|---|---|---|
| 2,773,501 A | 12/1956 | Young | 128/221 |
| 3,104,448 A | 9/1963 | Morrow et al. | |
| 3,120,845 A | 2/1964 | Horner | 128/310 |
| 3,173,417 A | 3/1965 | Horner | 128/305 |
| 3,175,554 A | 3/1965 | Stewart | 128/2 |
| 3,507,276 A | 4/1970 | Burgess et al. | 128/173 |
| 3,529,580 A | 8/1970 | Stevens | 122/406 |
| 3,543,966 A | 12/1970 | Ryan et al. | 222/94 |
| 3,750,667 A | 8/1973 | Pshenichny | 604/117 |
| 3,815,605 A | 6/1974 | Schmidt et al. | 128/305 |
| 3,835,860 A | 9/1974 | Garreston et al. | 128/310 |
| 3,893,445 A | 7/1975 | Hofsess | 128/2 |
| 3,981,398 A | 9/1976 | Boshoff | 206/223 |
| 3,991,765 A | 11/1976 | Cohen | 128/305 |
| 4,021,920 A | 5/1977 | Kirschner et al. | 32/28 |
| 4,046,254 A | 9/1977 | Kramer | 206/370 |
| 4,099,518 A | 7/1978 | Baylis et al. | 600/567 |
| 4,124,026 A | 11/1978 | Berner et al. | 606/104 |
| 4,142,517 A | 3/1979 | Stavropoulos et al. | 128/2 B |
| 4,170,993 A | 10/1979 | Alvarez | 128/214 R |
| 4,185,619 A | 1/1980 | Reiss | 128/1.1 |
| 4,194,505 A | 3/1980 | Schmitz | 128/218 |
| 4,258,722 A | 3/1981 | Sessions et al. | 128/753 |
| 4,262,676 A | 4/1981 | Jamshidi | 128/753 |
| 4,266,555 A | 5/1981 | Jamshidi | 600/566 |
| 4,306,570 A | 12/1981 | Matthews | 128/754 |
| 4,333,459 A | 6/1982 | Becker | 128/218 |
| 4,359,052 A | 11/1982 | Staub | 606/30 |
| 4,381,777 A | 5/1983 | Garnier | 604/188 |
| 4,399,723 A | 8/1983 | Marleau | 81/437 |
| 4,441,163 A | 4/1984 | Walton, II | 173/163 |
| 4,469,109 A | 9/1984 | Mehl | 128/753 |
| 4,484,577 A | 11/1984 | Sackner et al. | 128/203.28 |
| 4,487,209 A | 12/1984 | Mehl | 600/567 |
| 4,543,966 A | 10/1985 | Islam et al. | 128/754 |
| 4,553,539 A | 11/1985 | Morris | 128/132 D |
| 4,578,064 A * | 3/1986 | Sarnoff et al. | 604/191 |
| 4,605,011 A | 8/1986 | Naslund | 128/752 |
| 4,620,539 A | 11/1986 | Andrews et al. | 128/303 |
| 4,646,731 A | 3/1987 | Brower | 128/156 |
| 4,654,492 A | 3/1987 | Koerner et al. | 200/153 |
| 4,655,226 A | 4/1987 | Lee | 28/754 |
| 4,659,329 A | 4/1987 | Annis | 604/180 |
| 4,692,073 A | 9/1987 | Martindell | |
| 4,711,636 A | 12/1987 | Bierman | 604/180 |
| 4,713,061 A | 12/1987 | Tarello et al. | 604/200 |
| 4,716,901 A | 1/1988 | Jackson et al. | 128/343 |
| 4,720,881 A | 1/1988 | Meyers | 5/640 |
| 4,723,945 A | 2/1988 | Theiling | 604/232 |
| 4,758,225 A | 7/1988 | Cox et al. | 604/126 |
| 4,762,118 A | 8/1988 | Lia et al. | 128/4 |
| 4,772,261 A | 9/1988 | Von Hoff et al. | 604/51 |
| 4,787,893 A * | 11/1988 | Villette | 604/188 |
| 4,793,363 A | 12/1988 | Ausherman et al. | 128/754 |
| 4,838,282 A | 6/1989 | Strasser et al. | 600/567 |
| 4,844,259 A | 7/1989 | Glowczewskie, Jr. et al. | 206/370 |
| 4,867,158 A | 9/1989 | Sugg | 128/305 |
| 4,919,146 A | 4/1990 | Rhinehart et al. | 128/752 |
| 4,921,013 A | 5/1990 | Spalink et al. | 137/614.05 |
| 4,922,602 A | 5/1990 | Mehl | 29/460 |
| 4,935,010 A | 6/1990 | Cox et al. | 604/122 |
| 4,940,459 A | 7/1990 | Noce | 604/98 |
| 4,944,677 A | 7/1990 | Alexandre | 433/165 |
| 4,969,870 A | 11/1990 | Kramer et al. | 604/51 |
| 4,986,279 A | 1/1991 | O'Neill | 128/754 |
| 5,002,546 A | 3/1991 | Romano | 606/80 |
| 5,025,797 A | 6/1991 | Baran | 128/754 |
| 5,036,860 A | 8/1991 | Leigh et al. | 128/754 |
| 5,057,085 A | 10/1991 | Kopans | 604/173 |
| 5,074,311 A | 12/1991 | Hasson | 128/754 |
| 5,116,324 A | 5/1992 | Brierley et al. | 604/180 |
| 5,120,312 A | 6/1992 | Wigness et al. | 604/175 |
| 5,122,114 A | 6/1992 | Miller et al. | 604/49 |
| 5,133,359 A | 7/1992 | Kadem | 600/567 |
| 5,137,518 A | 8/1992 | Mersch | 604/168 |
| 5,139,500 A | 8/1992 | Schwartz | 606/96 |
| RE34,056 E | 9/1992 | Lindgren et al. | 128/754 |
| 5,145,369 A | 9/1992 | Lustig et al. | 433/118 |
| 5,172,701 A | 12/1992 | Leigh et al. | 128/753 |
| 5,172,702 A | 12/1992 | Leigh et al. | 128/754 |
| 5,176,415 A | 1/1993 | Choksi | 285/331 |
| 5,176,643 A | 1/1993 | Kramer et al. | 604/135 |
| 5,195,985 A | 3/1993 | Hall | 604/195 |
| 5,203,056 A | 4/1993 | Funk et al. | 24/543 |
| 5,207,697 A | 5/1993 | Carusillo et al. | 606/167 |
| 5,244,619 A | 9/1993 | Burnham | 264/171.2 |
| 5,249,583 A | 10/1993 | Mallaby | 128/754 |
| 5,257,632 A | 11/1993 | Turkel et al. | 128/754 |
| 5,261,877 A | 11/1993 | Fine et al. | 604/540 |
| 5,269,785 A | 12/1993 | Bonutti | 606/80 |
| 5,271,414 A | 12/1993 | Partika et al. | 600/567 |
| 5,279,306 A | 1/1994 | Mehl | 128/753 |
| 5,312,364 A | 5/1994 | Jacobs | 604/180 |
| 5,312,408 A | 5/1994 | Brown | 606/80 |
| 5,315,737 A | 5/1994 | Ouimet | 24/274 R |
| 5,324,300 A | 6/1994 | Elias et al. | 606/180 |
| 5,332,398 A | 7/1994 | Miller et al. | 604/175 |
| 5,333,790 A | 8/1994 | Christopher | 239/391 |
| 5,334,169 A | 8/1994 | Brown et al. | 604/527 |
| 5,341,816 A | 8/1994 | Allen | 600/567 |
| 5,341,823 A | 8/1994 | Manosalva et al. | 128/898 |
| 5,348,022 A | 9/1994 | Leigh et al. | 128/753 |
| 5,356,006 A * | 10/1994 | Alpern et al. | 206/363 |
| 5,357,974 A | 10/1994 | Baldridge | 128/754 |
| 5,368,046 A | 11/1994 | Scarfone et al. | 128/754 |
| 5,372,583 A * | 12/1994 | Roberts et al. | 604/506 |
| 5,383,859 A | 1/1995 | Sewell, Jr. | 604/164 |
| 5,385,151 A | 1/1995 | Scarfone et al. | 600/567 |
| 5,385,553 A | 1/1995 | Hart et al. | 604/167 |
| 5,400,798 A | 3/1995 | Baran | 128/754 |
| 5,405,348 A | 4/1995 | Anspach et al. | 606/80 |
| 5,405,362 A | 4/1995 | Kramer et al. | 607/5 |
| 5,423,824 A | 6/1995 | Akerfeldt et al. | 606/80 |
| 5,431,655 A | 7/1995 | Melker et al. | 606/79 |
| 5,451,210 A * | 9/1995 | Kramer et al. | 604/137 |
| 5,484,442 A | 1/1996 | Melker et al. | 606/79 |
| D369,858 S | 5/1996 | Baker et al. | D24/112 |
| 5,514,097 A | 5/1996 | Knauer | 604/136 |
| 5,526,821 A | 6/1996 | Jamshidi | 128/753 |
| 5,529,580 A | 6/1996 | Kusunoki et al. | 606/170 |
| 5,549,565 A | 8/1996 | Ryan et al. | 604/167 |
| 5,554,154 A * | 9/1996 | Rosenberg | 606/80 |
| 5,556,399 A | 9/1996 | Huebner et al. | 606/80 |
| 5,558,737 A | 9/1996 | Brown et al. | 156/172 |
| 5,571,133 A | 11/1996 | Yoon | 606/185 |
| 5,586,847 A | 12/1996 | Mattern, Jr. et al. | 408/239 A |
| 5,591,188 A | 1/1997 | Waisman | 606/182 |
| 5,595,186 A | 1/1997 | Rubinstein et al. | 600/567 |
| 5,601,559 A | 2/1997 | Melker et al. | 606/79 |
| 5,632,747 A | 5/1997 | Scarborough et al. | 606/79 |
| 5,672,155 A | 9/1997 | Riley et al. | 604/154 |
| 5,713,368 A | 2/1998 | Leigh | 128/753 |
| 5,724,873 A | 3/1998 | Hillinger | 81/451 |
| 5,733,262 A | 3/1998 | Paul | 604/116 |
| 5,752,923 A | 5/1998 | Terwilliger | 600/562 |
| 5,762,639 A | 6/1998 | Gibbs | 604/272 |
| 5,766,221 A | 6/1998 | Benderev et al. | 606/232 |
| 5,769,086 A | 6/1998 | Ritchart et al. | 128/753 |
| 5,779,708 A | 7/1998 | Wu | 606/80 |
| 5,800,389 A | 9/1998 | Burney et al. | 604/93 |
| 5,807,275 A | 9/1998 | Jamshidi | 600/567 |
| 5,807,277 A | 9/1998 | Swaim | 600/567 |
| 5,810,826 A | 9/1998 | Akerfeldt et al. | 606/80 |
| 5,817,052 A | 10/1998 | Johnson et al. | 604/51 |
| 5,823,970 A | 10/1998 | Terwilliger | 600/564 |
| D403,405 S | 12/1998 | Terwilliger | D24/130 |
| 5,858,005 A | 1/1999 | Kriesel | 604/180 |

(56) References Cited

U.S. PATENT DOCUMENTS

| | | | |
|---|---|---|---|
| 5,868,711 A | 2/1999 | Kramer et al. | 604/136 |
| 5,868,750 A | 2/1999 | Schultz | 606/104 |
| 5,873,499 A | 2/1999 | Leschinsky et al. | 222/327 |
| 5,873,510 A | 2/1999 | Hirai et al. | 227/130 |
| 5,885,226 A | 3/1999 | Rubinstein et al. | 600/564 |
| 5,891,085 A | 4/1999 | Lilley et al. | 604/68 |
| 5,906,797 A | 5/1999 | Orihara et al. | 422/177 |
| 5,911,701 A | 6/1999 | Miller et al. | 604/22 |
| 5,911,708 A | 6/1999 | Teirstein | 604/183 |
| 5,916,229 A | 6/1999 | Evans | 606/171 |
| 5,919,172 A | 7/1999 | Golba, Jr. | 604/272 |
| 5,921,987 A | 7/1999 | Stone | 606/80 |
| 5,924,864 A | 7/1999 | Loge et al. | 433/118 |
| 5,926,989 A | 7/1999 | Oliver, Sr. | 42/70.11 |
| 5,927,976 A | 7/1999 | Wu | 433/82 |
| 5,928,238 A | 7/1999 | Scarborough et al. | 606/79 |
| 5,941,706 A | 8/1999 | Ura | 433/165 |
| 5,941,851 A | 8/1999 | Coffey et al. | 604/131 |
| 5,951,026 A | 9/1999 | Harman, Jr. et al. | 279/143 |
| 5,960,797 A * | 10/1999 | Kramer et al. | 128/899 |
| 5,980,545 A | 11/1999 | Pacala et al. | 606/170 |
| 5,993,417 A | 11/1999 | Yerfino et al. | 604/110 |
| 5,993,454 A | 11/1999 | Longo | 606/80 |
| 6,007,496 A | 12/1999 | Brannon | 600/565 |
| 6,017,348 A | 1/2000 | Hart et al. | 606/79 |
| 6,018,094 A | 1/2000 | Fox | 623/11 |
| 6,018,230 A | 1/2000 | Casey | 320/114 |
| 6,022,324 A | 2/2000 | Skinner | 600/566 |
| 6,027,458 A | 2/2000 | Janssens | 600/567 |
| 6,033,369 A | 3/2000 | Goldenberg | 600/567 |
| 6,033,411 A | 3/2000 | Preissman | 606/99 |
| 6,042,585 A | 3/2000 | Norman | 606/104 |
| 6,049,725 A | 4/2000 | Emmert et al. | 455/573 |
| 6,063,037 A | 5/2000 | Mittermeier et al. | 600/567 |
| 6,066,938 A | 5/2000 | Hyodo et al. | 320/114 |
| 6,071,284 A | 6/2000 | Fox | 606/80 |
| 6,080,115 A | 6/2000 | Rubinstein | 600/567 |
| 6,083,176 A | 7/2000 | Terwilliger | 600/562 |
| 6,086,543 A | 7/2000 | Anderson et al. | 600/567 |
| 6,086,544 A | 7/2000 | Hibner et al. | 600/568 |
| 6,096,042 A | 8/2000 | Herbert | 606/80 |
| 6,102,915 A | 8/2000 | Bersler et al. | 606/80 |
| 6,106,484 A | 8/2000 | Terwilliger | 600/568 |
| 6,110,128 A | 8/2000 | Andelin et al. | 600/566 |
| 6,110,129 A | 8/2000 | Terwilliger | 600/567 |
| 6,110,174 A | 8/2000 | Nichter | 606/72 |
| 6,120,462 A | 9/2000 | Hibner et al. | 600/566 |
| 6,135,769 A | 10/2000 | Kwan | 433/80 |
| 6,152,918 A | 11/2000 | Padilla et al. | 606/15 |
| 6,159,163 A | 12/2000 | Strauss et al. | 600/566 |
| 6,162,203 A | 12/2000 | Haaga | 604/272 |
| 6,183,442 B1 * | 2/2001 | Athanasiou et al. | 604/154 |
| 6,187,768 B1 * | 2/2001 | Welle et al. | 514/199 |
| 6,210,376 B1 | 4/2001 | Grayson | 604/264 |
| 6,217,561 B1 * | 4/2001 | Gibbs | 604/264 |
| 6,221,029 B1 | 4/2001 | Mathis et al. | 600/564 |
| 6,228,049 B1 | 5/2001 | Schroeder et al. | 604/93.01 |
| 6,228,088 B1 | 5/2001 | Miller et al. | 606/80 |
| 6,238,355 B1 | 5/2001 | Daum | 600/567 |
| 6,247,928 B1 | 6/2001 | Meller et al. | 433/80 |
| 6,248,110 B1 | 6/2001 | Reiley et al. | 606/93 |
| 6,257,351 B1 | 7/2001 | Ark et al. | 173/178 |
| 6,267,763 B1 | 7/2001 | Castro | 606/86 |
| 6,273,715 B1 | 8/2001 | Meller et al. | 433/80 |
| 6,273,862 B1 | 8/2001 | Privitera et al. | 600/568 |
| 6,283,925 B1 | 9/2001 | Terwilliger | 600/568 |
| 6,283,970 B1 | 9/2001 | Lubinus | 606/80 |
| 6,287,114 B1 | 9/2001 | Meller et al. | 433/80 |
| 6,302,852 B1 | 10/2001 | Fleming, III et al. | 600/567 |
| 6,309,358 B1 | 10/2001 | Okubo | 600/466 |
| 6,312,394 B1 | 11/2001 | Fleming, III | 600/567 |
| 6,315,737 B1 | 11/2001 | Skinner | 600/566 |
| 6,325,806 B1 | 12/2001 | Fox | 606/80 |
| 6,328,701 B1 | 12/2001 | Terwilliger | 600/567 |
| 6,328,744 B1 | 12/2001 | Harari et al. | 606/80 |
| 6,358,252 B1 | 3/2002 | Shapira | 606/80 |
| 6,382,212 B1 | 5/2002 | Borchard | 128/849 |
| 6,402,701 B1 | 6/2002 | Kaplan et al. | 600/567 |
| 6,419,490 B1 | 7/2002 | Kitchings Weathers, Jr. | 433/165 |
| 6,425,888 B1 | 7/2002 | Embleton et al. | 604/290 |
| 6,428,487 B1 | 8/2002 | Burdorff et al. | 600/568 |
| 6,443,910 B1 | 9/2002 | Krueger et al. | 600/567 |
| 6,458,117 B1 | 10/2002 | Pollins, Sr. | 604/523 |
| 6,468,248 B1 | 10/2002 | Gibbs | 604/164.01 |
| 6,478,751 B1 | 11/2002 | Krueger et al. | 600/566 |
| 6,488,636 B1 | 12/2002 | Bryan et al. | 600/565 |
| 6,523,698 B1 | 2/2003 | Dennehey et al. | 210/435 |
| 6,527,736 B1 | 3/2003 | Attinger et al. | 604/43 |
| 6,527,778 B2 | 3/2003 | Athanasiou et al. | 606/80 |
| 6,540,694 B1 | 4/2003 | Van Bladel et al. | 600/564 |
| 6,547,511 B1 | 4/2003 | Adams | 414/46.4 |
| 6,547,561 B2 | 4/2003 | Meller et al. | 433/80 |
| 6,550,786 B2 | 4/2003 | Gifford et al. | 279/75 |
| 6,554,779 B2 | 4/2003 | Viola et al. | 600/568 |
| 6,555,212 B2 | 4/2003 | Boiocchi et al. | 428/295.4 |
| 6,572,563 B2 | 6/2003 | Ouchi | 600/564 |
| 6,575,919 B1 | 6/2003 | Reiley et al. | 600/567 |
| 6,582,399 B1 | 6/2003 | Smith et al. | 604/152 |
| 6,585,622 B1 | 7/2003 | Shum et al. | 482/8 |
| 6,595,362 B2 * | 7/2003 | Penney et al. | 206/364 |
| 6,595,911 B2 | 7/2003 | LoVuolo | 600/30 |
| 6,595,979 B1 | 7/2003 | Epstein et al. | 604/506 |
| 6,613,054 B2 | 9/2003 | Scribner et al. | 606/93 |
| 6,616,632 B2 | 9/2003 | Sharp et al. | 604/117 |
| 6,620,111 B2 | 9/2003 | Stephens et al. | 600/567 |
| 6,626,173 B2 | 9/2003 | Genova et al. | 128/203.15 |
| 6,626,848 B2 | 9/2003 | Nueenfeldt | 600/564 |
| 6,626,887 B1 | 9/2003 | Wu | 604/512 |
| 6,638,235 B2 | 10/2003 | Miller et al. | 600/566 |
| 6,656,133 B2 | 12/2003 | Voegele et al. | 600/568 |
| 6,689,072 B2 | 2/2004 | Kaplan et al. | 600/567 |
| 6,690,308 B2 | 2/2004 | Hayami | 341/68 |
| 6,702,760 B2 | 3/2004 | Krause et al. | 600/564 |
| 6,702,761 B1 | 3/2004 | Damadian et al. | 600/576 |
| 6,706,016 B2 | 3/2004 | Cory et al. | 604/117 |
| 6,716,192 B1 | 4/2004 | Orosz, Jr. | 604/117 |
| 6,716,215 B1 | 4/2004 | David et al. | 606/80 |
| 6,716,216 B1 | 4/2004 | Boucher et al. | 606/86 |
| 6,730,043 B2 | 5/2004 | Krueger et al. | 600/567 |
| 6,730,044 B2 | 5/2004 | Stephens et al. | 600/568 |
| 6,749,576 B2 | 6/2004 | Bauer | 600/567 |
| 6,752,768 B2 | 6/2004 | Burdorff et al. | 600/568 |
| 6,752,816 B2 | 6/2004 | Culp et al. | 606/170 |
| 6,758,824 B1 | 7/2004 | Miller et al. | 600/568 |
| 6,761,726 B1 * | 7/2004 | Findlay et al. | 606/182 |
| 6,796,957 B2 | 9/2004 | Carpenter et al. | 604/93.01 |
| 6,846,314 B2 | 1/2005 | Shapira | 606/80 |
| 6,849,051 B2 | 2/2005 | Sramek et al. | 600/565 |
| 6,855,148 B2 | 2/2005 | Foley et al. | 606/86 |
| 6,860,860 B2 | 3/2005 | Viola | 600/564 |
| 6,875,183 B2 | 4/2005 | Cervi | 600/567 |
| 6,875,219 B2 | 4/2005 | Arramon et al. | 606/92 |
| 6,884,245 B2 | 4/2005 | Spranza | 606/79 |
| 6,887,209 B2 | 5/2005 | Kadziauskas et al. | 600/565 |
| 6,890,308 B2 | 5/2005 | Islam | 600/564 |
| 6,896,141 B2 * | 5/2005 | McMichael et al. | 206/571 |
| 6,905,486 B2 | 6/2005 | Gibbs | 604/264 |
| 6,930,461 B2 | 8/2005 | Rutkowski | 318/567 |
| 6,942,669 B2 | 9/2005 | Kurc | 606/80 |
| 6,969,373 B2 | 11/2005 | Schwartz et al. | 604/170.03 |
| 7,001,342 B2 | 2/2006 | Faciszewski | 600/564 |
| 7,008,381 B2 | 3/2006 | Janssens | 600/564 |
| 7,008,383 B1 | 3/2006 | Damadian et al. | 600/567 |
| 7,008,394 B2 | 3/2006 | Geise et al. | 615/6.15 |
| 7,018,343 B2 | 3/2006 | Plishka | 600/564 |
| 7,025,732 B2 | 4/2006 | Thompson et al. | 600/654 |
| 7,063,672 B2 | 6/2006 | Schramm | 600/564 |
| 7,063,703 B2 | 6/2006 | Reo | 606/79 |
| 7,137,985 B2 | 11/2006 | Jahng | 606/61 |
| 7,186,257 B2 | 3/2007 | Kim | 606/96 |
| 7,207,949 B2 | 4/2007 | Miles et al. | 600/554 |
| 7,226,450 B2 | 6/2007 | Athanasiou et al. | 606/80 |
| 7,229,401 B2 | 6/2007 | Kindlein | 600/7 |
| 7,278,972 B2 | 10/2007 | Lamoureux et al. | 600/567 |

(56) References Cited

U.S. PATENT DOCUMENTS

| | | | |
|---|---|---|---|
| 7,331,462 B2* | 2/2008 | Steppe | 206/570 |
| 7,331,930 B2 | 2/2008 | Faciszewski | 600/567 |
| 7,513,722 B2 | 4/2009 | Greenberg et al. | 408/202 |
| 7,615,043 B2 | 11/2009 | Zhou | 604/523 |
| 7,670,328 B2 | 3/2010 | Miller | 604/506 |
| 7,699,850 B2 | 4/2010 | Miller | 606/80 |
| 7,811,260 B2 | 10/2010 | Miller et al. | 604/188 |
| 7,815,642 B2 | 10/2010 | Miller | 606/79 |
| 7,850,620 B2 | 12/2010 | Miller et al. | 600/568 |
| 7,951,089 B2 | 5/2011 | Miller | 600/566 |
| 7,988,643 B2 | 8/2011 | Hoffmann et al. | 600/567 |
| 8,038,664 B2 | 10/2011 | Miller et al. | 604/506 |
| 8,217,561 B2 | 7/2012 | Fukuzawa | 313/141 |
| 8,419,683 B2 | 4/2013 | Miller et al. | 604/117 |
| 8,480,632 B2 | 7/2013 | Miller et al. | 604/188 |
| 8,506,568 B2 | 8/2013 | Miller | 606/80 |
| 8,641,715 B2 | 2/2014 | Miller | 606/80 |
| 8,656,929 B2 | 2/2014 | Miller et al. | 128/898 |
| 8,668,698 B2 | 3/2014 | Miller et al. | 606/80 |
| 8,684,978 B2 | 4/2014 | Miller et al. | 604/235 |
| 8,690,791 B2 | 4/2014 | Miller | 600/562 |
| 8,715,287 B2 | 5/2014 | Miller | 606/80 |
| 2001/0005778 A1 | 6/2001 | Ouchi | 600/564 |
| 2001/0014439 A1 | 8/2001 | Meller et al. | 433/50 |
| 2001/0047183 A1 | 11/2001 | Privitera et al. | 606/170 |
| 2001/0053888 A1 | 12/2001 | Athanasiou et al. | 604/154 |
| 2002/0042581 A1 | 4/2002 | Cervi | 600/567 |
| 2002/0055713 A1 | 5/2002 | Gibbs | 604/164.01 |
| 2002/0120212 A1 | 8/2002 | Ritchart et al. | 600/567 |
| 2002/0138021 A1 | 9/2002 | Pflueger | 600/565 |
| 2003/0028146 A1 | 2/2003 | Aves | 604/164.06 |
| 2003/0032939 A1 | 2/2003 | Gibbs | 604/510 |
| 2003/0036747 A1 | 2/2003 | Ie et al. | 606/1 |
| 2003/0050574 A1 | 3/2003 | Krueger | 600/567 |
| 2003/0114858 A1 | 6/2003 | Athanasiou et al. | 606/80 |
| 2003/0125639 A1 | 7/2003 | Fisher et al. | 600/564 |
| 2003/0153842 A1 | 8/2003 | Lamoureux et al. | 600/564 |
| 2003/0191414 A1 | 10/2003 | Reiley et al. | 600/567 |
| 2003/0195436 A1 | 10/2003 | Van Bladel et al. | 600/584 |
| 2003/0195524 A1 | 10/2003 | Barner | 606/119 |
| 2003/0199787 A1 | 10/2003 | Schwindt | 600/568 |
| 2003/0216667 A1 | 11/2003 | Viola | 600/564 |
| 2003/0225344 A1 | 12/2003 | Miller | 600/568 |
| 2003/0225364 A1 | 12/2003 | Kraft et al. | 604/35 |
| 2003/0225411 A1 | 12/2003 | Miller | 606/80 |
| 2004/0019297 A1 | 1/2004 | Angel | 600/564 |
| 2004/0019299 A1 | 1/2004 | Ritchart et al. | 600/567 |
| 2004/0034280 A1 | 2/2004 | Privitera et al. | 600/170 |
| 2004/0049128 A1 | 3/2004 | Miller et al. | 600/566 |
| 2004/0064136 A1 | 4/2004 | Papineau et al. | 606/41 |
| 2004/0073139 A1 | 4/2004 | Hirsch et al. | 600/564 |
| 2004/0092946 A1 | 5/2004 | Bagga et al. | 606/93 |
| 2004/0127814 A1 | 7/2004 | Negroni | 600/567 |
| 2004/0153003 A1 | 8/2004 | Cicenas et al. | 600/564 |
| 2004/0158172 A1 | 8/2004 | Hacock | 600/564 |
| 2004/0158173 A1 | 8/2004 | Voegele et al. | 600/568 |
| 2004/0162505 A1 | 8/2004 | Kaplan et al. | 600/567 |
| 2004/0191897 A1 | 9/2004 | Muschler | 435/325 |
| 2004/0210161 A1 | 10/2004 | Burdorff et al. | 600/566 |
| 2004/0210198 A1 | 10/2004 | Shih | 604/218 |
| 2004/0215102 A1 | 10/2004 | Ikehara et al. | 600/562 |
| 2004/0220497 A1 | 11/2004 | Findlay et al. | 600/562 |
| 2005/0027210 A1 | 2/2005 | Miller | 600/567 |
| 2005/0040060 A1 | 2/2005 | Andersen et al. | 206/363 |
| 2005/0075581 A1 | 4/2005 | Schwindt | 600/568 |
| 2005/0085838 A1 | 4/2005 | Thompson et al. | 606/170 |
| 2005/0101880 A1 | 5/2005 | Cicenas et al. | 600/567 |
| 2005/0113716 A1 | 5/2005 | Mueller et al. | 600/564 |
| 2005/0119660 A1 | 6/2005 | Bourlion et al. | 606/80 |
| 2005/0124915 A1 | 6/2005 | Eggers et al. | 600/568 |
| 2005/0131345 A1 | 6/2005 | Miller | 604/117 |
| 2005/0148940 A1 | 7/2005 | Miller | 604/187 |
| 2005/0165328 A1 | 7/2005 | Heske et al. | 600/566 |
| 2005/0165403 A1 | 7/2005 | Miller | 606/79 |
| 2005/0165404 A1 | 7/2005 | Miller | 606/80 |
| 2005/0171504 A1 | 8/2005 | Miller | 604/506 |
| 2005/0182394 A1 | 8/2005 | Spero et al. | 606/21 |
| 2005/0200087 A1* | 9/2005 | Vasudeva et al. | 279/143 |
| 2005/0203439 A1 | 9/2005 | Heske et al. | 600/566 |
| 2005/0209530 A1 | 9/2005 | Pflueger | 600/567 |
| 2005/0215921 A1 | 9/2005 | Hibner et al. | 600/566 |
| 2005/0228309 A1 | 10/2005 | Fisher et al. | 600/562 |
| 2005/0236940 A1 | 10/2005 | Rockoff | 312/209 |
| 2005/0261693 A1 | 11/2005 | Miller et al. | 606/80 |
| 2006/0011506 A1 | 1/2006 | Riley | 206/570 |
| 2006/0015066 A1* | 1/2006 | Turieo et al. | 604/136 |
| 2006/0036212 A1 | 2/2006 | Miller | 604/48 |
| 2006/0052790 A1 | 3/2006 | Miller | 606/80 |
| 2006/0074345 A1 | 4/2006 | Hibner | 600/566 |
| 2006/0079774 A1 | 4/2006 | Anderson | 600/442 |
| 2006/0089565 A1 | 4/2006 | Schramm | 600/568 |
| 2006/0122535 A1 | 6/2006 | Daum | 600/565 |
| 2006/0129082 A1 | 6/2006 | Rozga | 604/6.04 |
| 2006/0144548 A1 | 7/2006 | Beckman et al. | 163/1 |
| 2006/0149163 A1 | 7/2006 | Hibner et al. | 600/566 |
| 2006/0167377 A1 | 7/2006 | Ritchart et al. | 600/566 |
| 2006/0167378 A1 | 7/2006 | Miller | 600/566 |
| 2006/0167379 A1 | 7/2006 | Miller | 600/566 |
| 2006/0184063 A1 | 8/2006 | Miller | 600/568 |
| 2006/0189940 A1 | 8/2006 | Kirsch | 604/164.1 |
| 2006/0206132 A1 | 9/2006 | Conquergood et al. | 606/180 |
| 2007/0016100 A1 | 1/2007 | Miller | 600/567 |
| 2007/0049945 A1 | 3/2007 | Miller | 606/86 |
| 2007/0149920 A1 | 6/2007 | Michels et al. | 604/93.01 |
| 2007/0213735 A1 | 9/2007 | Sandat et al. | 606/79 |
| 2007/0270775 A1 | 11/2007 | Miller et al. | 604/506 |
| 2008/0015467 A1 | 1/2008 | Miller | 600/568 |
| 2008/0015468 A1 | 1/2008 | Miller | 600/568 |
| 2008/0045857 A1 | 2/2008 | Miller et al. | 600/566 |
| 2008/0045860 A1 | 2/2008 | Miller et al. | 600/567 |
| 2008/0045861 A1 | 2/2008 | Miller et al. | 600/567 |
| 2008/0045965 A1 | 2/2008 | Miller et al. | 606/80 |
| 2008/0140014 A1 | 6/2008 | Miller et al. | 604/180 |
| 2008/0177200 A1 | 7/2008 | Ikehara et al. | 600/567 |
| 2008/0215056 A1 | 9/2008 | Miller et al. | 606/80 |
| 2008/0221580 A1 | 9/2008 | Miller et al. | 606/80 |
| 2009/0069716 A1 | 3/2009 | Freeman et al. | 600/583 |
| 2009/0093677 A1 | 4/2009 | Smith | 600/114 |
| 2009/0194446 A1 | 8/2009 | Miller et al. | 206/438 |
| 2010/0204611 A1 | 8/2010 | Zambelli | 600/567 |
| 2011/0046507 A1 | 2/2011 | Herndon | 600/547 |
| 2011/0082387 A1 | 4/2011 | Miller et al. | 600/567 |
| 2011/0306841 A1 | 12/2011 | Lozman et al. | 600/204 |
| 2012/0165832 A1 | 6/2012 | Oostman, Jr. et al. | 606/131 |

FOREIGN PATENT DOCUMENTS

| | | | |
|---|---|---|---|
| CN | 2320209 | 5/1999 | |
| CN | 2664675 | 12/2004 | |
| DE | 10057931 | 11/2000 | |
| EP | 0517000 | 5/1992 | |
| EP | 0807412 | 11/1997 | |
| EP | 0807412 A1 | 11/1997 | A61B 17/32 |
| EP | 1099450 | 11/1997 | |
| EP | 1314452 | 5/2003 | |
| EP | 1421907 | 5/2004 | |
| EP | 1447050 | 8/2004 | |
| FR | 853349 | 3/1940 | |
| FR | 2457105 | 5/1979 | A61M 5/00 |
| FR | 2516386 | 11/1981 | A61M 5/18 |
| GB | 2130890 A | 6/1984 | A61B 10/00 |
| JP | 59119808 | 8/1984 | |
| JP | 6132663 | 9/1986 | |
| JP | 1052433 | 2/1989 | |
| JP | 2001505076 | 4/2001 | |
| WO | WO 9208410 | 5/1992 | |
| WO | 93/07819 | 4/1993 | A61B 17/32 |
| WO | 96/31164 | 10/1996 | A61B 17/34 |
| WO | 98/06337 | 2/1998 | A61B 17/16 |
| WO | WO 9852638 | 11/1998 | |
| WO | WO 9918866 | 4/1999 | |
| WO | 99/52444 | 10/1999 | A61B 17/00 |
| WO | WO 0009024 | 2/2000 | |
| WO | WO 0056220 | 9/2000 | |

(56) References Cited

FOREIGN PATENT DOCUMENTS

| | | | |
|---|---|---|---|
| WO | WO 0178590 | 10/2001 | |
| WO | 02/41792 A1 | 5/2002 | ............ A61B 17/16 |
| WO | WO 0241792 | 5/2002 | |
| WO | WO 02096497 | 12/2002 | |
| WO | WO 03015637 | 2/2003 | |
| WO | WO 2005072625 | 8/2005 | |
| WO | WO 2005110259 | 11/2005 | |
| WO | 2005/112800 | 12/2005 | ............ A61B 17/34 |
| WO | WO 2008033874 | 3/2008 | |
| WO | WO 2008081438 | 7/2008 | |
| WO | WO 2011123703 | 10/2011 | |

OTHER PUBLICATIONS

Pediatrics, "2005 American Heart Association Guidelines for Cardiopulmonary Resuscitation and Emergency Cardiovascular Care of Pediatric and Neonatal Patients: Pediatric Advanced Life Support," www.pediatrics.org, Official Journal of the American Academy of Pediatrics (26 pages), Feb. 21, 2007.
Official Action for European Application No. 03756317.8 (4 pages), Dec. 28, 2006.
International Search Report and Written Opinion for International Application No. PCT/US2006/025201 (18 pages), Jan. 29, 2007.
International PCT Search Report PCT/US03/17167, 8 pages, Mailed Sep. 16, 2003.
International PCT Search Report PCT/US03/17203, 8 pages, Mailed Sep. 16, 2003.
International PCT Search Report PCT/US2004/037753, 6 pages, Mailed Apr. 19, 2005.
International PCT Search Report and Written Opinion PCT/US2004/037753, 16 pages, Mailed Jul. 8, 2005.
Cummins, Richard O., et al, "ACLS-Principles and Practice", ACLS—The Reference Textbook, American Heart Association, pp. 214-218, 2003.
International Preliminary Report on Patentability PCT/US2005/002484, 9 pages, Mailed Aug. 3, 2006.
Communication relating to the results of the partial International Search Report for PCT/US2005/002484, 6 pages, Mailed May 19, 2005.
Riley et al., "A Pathologist's Perspective on Bone Marrow Aspiration Biopsy: I. Performing a Bone Marrow Examination," Journal of Clinical Laboratory Analysis 18, pp. 70-90, 2004.
Australian Exam Report on Patent Application No. 2003240970, 2 pages, Oct. 15, 2007.
"Proven reliability for quality bone marrow samples", Special Procedures, Cardinal Health, 6 pages, 2003.
Åström, "Automatic Biopsy Instruments Used Through a Coaxial Bone Biopsy System with an Eccentric Drill Tip," Acta Radiologica 36: 237-242. May 1995.
Åström, "CT-guided Transsternal Core Biopsy of Anterior Mediastinal Masses," Radiology 199:564-567. May 1996.
BioAccess.com, Single Use Small Bone Power Tool —How It Works. Accessed Jun. 9, 2008.
Buckley et al., "CT-guided bone biopsy: initial experience with commercially available hand held Black and Decker drill," European Journal of Radiology 61:176-180. 2007.
F.A.S.T. 1 Intraosseous Infusion System with Depth-Control Mechanism Brochure. 2000.
Gunal et al., "Compartment Syndrome After Intraosseous Infusion: An Experimental Study in Dogs," *J of Pediatric Surgery* 31(11): 1491-1493. Nov. 1996.
Hakan et al., "CT-guided bone biopsy performed by means of coaxial biopsy system with an eccentric drill," *Radiology* 549-552. Aug. 1993.
Notice of Allowance in U.S. Appl. No. 11/042,912, mailed Sep. 24, 2013.
Notice of Allowance in U.S. Appl. No. 11/619,390 mailed Jul. 3, 2014.
Notice of Allowance in U.S. Appl. No. 11/620,927 mailed Jun. 3, 2014.
Notice of Allowance in U.S. Appl. No. 11/853,678 issued Jul. 11, 2013.
Notice of Allowance in U.S. Appl. No. 11/853,678, mailed Oct. 11, 2013.
Notice of Allowance in U.S. Appl. No. 11/853,678, mailed Nov. 8, 2013.
Notice of Allowance in U.S. Appl. No. 12/331,979, mailed Dec. 23, 2013.
Notice of Allowance in U.S. Appl. No. 12/407,651 mailed Jun. 11, 2014.
Notice of Allowance in U.S. Appl. No. 12/427,310, mailed Nov. 29, 2013.
Notice of Allowance in U.S. Appl. No. 12/899,696 issued Jul. 18, 2013.
Notice of Allowance in U.S. Patent Application No. 12/899,696, mailed Nov. 12, 2013.
Notice of Allowance in U.S. Appl. No. 14/721,144 mailed Jul. 22, 2014.
Notice of Allowance issued in U.S. Appl. No. 11/253,467, mailed Mar. 29, 2013.
Notice of Allowance issued in U.S. Appl. No. 11/253,959, mailed May 20, 2013.
Notice of Allowance issued on Mar. 4, 2014 in U.S. Appl. No. 11/253,467.
Office Action for U.S. Appl. No. 11/042,912. Mailed Mar. 19, 2010.
Office Action for U.S. Appl. No. 11/253,467. Mailed Apr. 28, 2011.
Office Action for U.S. Appl. No. 11/253,467. Mailed Jul. 22, 2010.
Office Action for U.S. Appl. No. 11/253,959. Mailed Mar. 30, 2011.
Office Action for U.S. Appl. No. 12/905,659. Dated Mar. 21, 2011.
Office Action for U.S. Appl. No. 12/905,659. Dated May 13, 2011.
Pediatric Emergency, Intraosseous Infusion for Administration of Fluids and Drugs, www.cookgroup.com, 1 pg, 2000.
Pediatrics, Official Journal of the American Academy of Pediatrics, "2005 American Heart Association Guidelines for Cardiopulmonary Resuscitation and Emergency Cardiovascular Care of Pediatric and Neonatal Patients: Pediatric Advanced Life Support", Downloaded from www.pediatrics.org, Feb. 21, 2007.
Riley et al., "A Pathologist's Perspective on Bone Marrow Aspiration Biopsy: I. Performing a Bone Marrow Examination," Journal of Clinical Laboratory Analysis 18, pp. 70-90, 2004.
U.S. Appl. No. 11/427,501 Non-Final Office Action, 14 pages, Mailed Aug. 7, 2008.
Vidacare Corporation Comments to Intraosseous Vascular Access Position Paper, Infusion Nurses Society, 6 pages, May 4, 2009.

\* cited by examiner

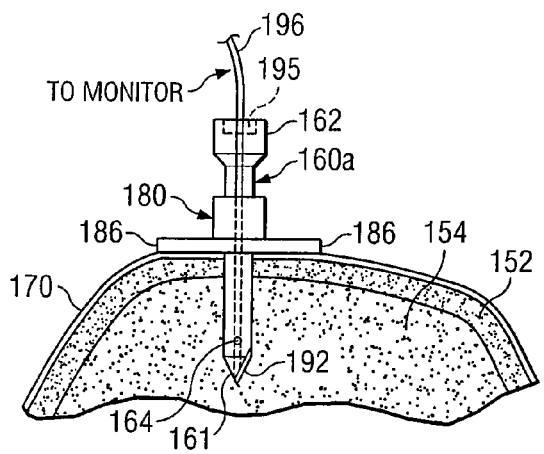
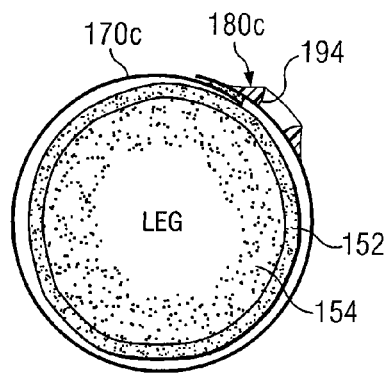
FIG. 13
FIG. 14
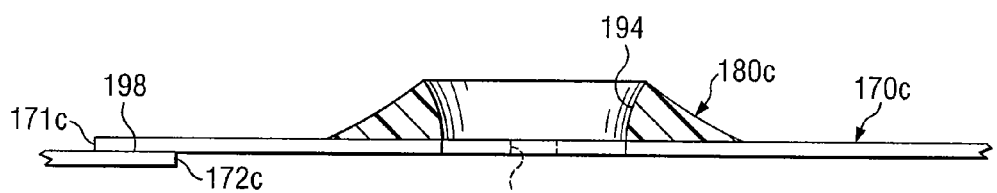
FIG. 15
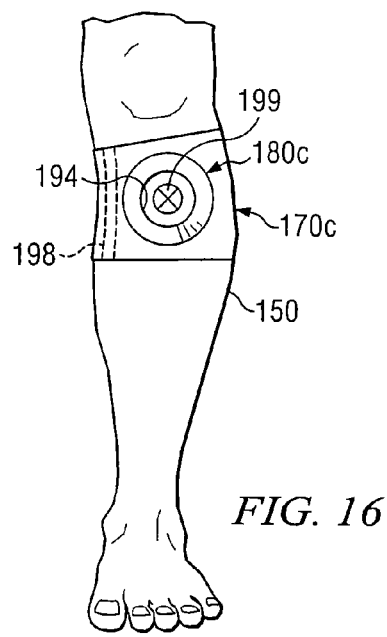
FIG. 16

VASCULAR ACCESS KITS AND METHODS

RELATED APPLICATION

This application claims the benefit of U.S. Provisional Patent Application Ser. No. 60/675,246, filed Apr. 27, 2005, and entitled "Vascular Access Kit."

This application is a U.S. continuation-in-part application of U.S. application Ser. No. 10/449,503 entitled "Apparatus And Method To Provide Emergency Access To Bone Marrow", filed May 30, 2003 now U.S. Pat. No. 7,670,328, which claims the benefit of U.S. Provisional Patent Application Ser. No. 60/384,756, filed May 31, 2002.

CROSS-REFERENCE TO RELATED APPLICATIONS

The present disclosure is related to U.S. patent application Ser. No. 10/449,503 filed May 30, 2003; U.S. patent application Ser. No. 10/448,650 filed May 30, 2003; U.S. patent application Ser. No. 10/449,476 filed May 30, 2003; and U.S. patent application Ser. No. 10/987,051 filed Nov. 12, 2004.

TECHNICAL FIELD

The present disclosure is related to apparatus and methods to obtain vascular access and more particularly to a kit, apparatus contained in the kit and associated methods which may be used to provide access to bone, bone marrow and other portions of a patient's vascular system using the apparatus.

BACKGROUND

Every year, millions of patients are treated for life threatening emergencies in the United States. Such emergencies include shock, trauma, cardiac arrest, drug overdoses, diabetic ketoacidosis, arrhythmias, burns, and status epilepticus just to name a few. For example, according to the American Heart Association, more than 1,500,000 patients suffer from heart attacks (myocardial infarctions) every year, with over 500,000 of them dying from its devastating complications. In addition, many wounded soldiers die unnecessarily because intravenous (IV) access cannot be achieved in a timely manner. Many soldiers die within an hour of injury, usually from severe bleeding and/or shock.

An essential element for treating all such emergencies may be the rapid establishment of an IV line in order to administer drugs and fluids directly into the circulatory system. Whether in the ambulance by paramedics, in the emergency room by emergency specialists or on the battlefield by an Army medic, a common goal is to start an IV as soon as possible to administer life saving drugs and fluids. To a large degree, the ability to successfully treat such critical emergencies may be dependent on the skill and luck of the operator in accomplishing vascular access. While it may be relatively easy to start an IV on some patients, doctors, nurses and paramedics often experience difficulty establishing IV access in approximately twenty (20%) percent of patients. The success rate on the battlefield is often much lower where Army medics may only be about twenty-nine (29%) percent successful in starting an IV line during emergency conditions in the field. These patients are probed repeatedly with sharp needles in an attempt to solve this problem and may require an invasive procedure to finally establish an intravenous route.

In the case of patients with chronic disease or the elderly, the availability of easily accessible veins may be depleted. Other patients may have no available IV sites due to anatomical scarcity of peripheral veins, obesity, extreme dehydration or previous IV drug use. For these patients, finding a suitable site for administering life saving drugs may become a difficult and frustrating task. It is generally well known that patients with life threatening emergencies have died because access to the patient's vascular system with life saving IV therapy was delayed or simply not possible.

An accepted alternative route to give IV medications and fluids is through bone marrow by providing intraosseous (IO) access. Drugs and other fluids may enter a patient's vascular system just as rapidly via the intraosseous route as when given intravenously. Bone and associated bone marrow may be considered a large, non-collapsible vein. The IO route has been used for alternative emergency access in pediatric patients, whose bones are soft enough to permit manual insertion of IO needles.

SUMMARY

The present disclosure relates to kits, apparatus contained in such kits and associated procedures to obtain access to a patient's vascular system. For some embodiments such kits may include intravenous (IV) access devices and intraosseous (IO) access devices. Such kits may be used in both emergency situations or more routine procedures associated with treating chronic conditions. The present disclosure may provide apparatus and methods to establish vascular access during treatment of a patient at a wide variety of locations and facilities including, but not limited to, accident sites, emergency rooms, battlefields, emergency medical services (EMS) facilities, oncology treatment centers, chronic disease treatment facilities and veterinary applications.

Technical benefits of some embodiments may include providing portable kits with devices and components for rapid penetration of bone and bone marrow to provide access to a patient's vascular system.

Technical benefits of some embodiments may include devices and components for rapid penetration of bone and associated bone marrow. Such devices and components may be placed in a kit for use in accessing a patient's vascular system.

Technical benefits of some embodiments may include obtaining fast, inexpensive access to a patient's vascular system with minimal risk. Apparatus and methods incorporating teachings of the present disclosure may be used to provide IO and IV access so that drugs and/or fluids can be injected into associated bone marrow.

BRIEF DESCRIPTION OF THE DRAWINGS

A more complete and thorough understanding of various embodiments and advantages thereof may be acquired by referring to the following description taken in conjunction with the accompanying drawings, in which like reference numbers indicate like features, and wherein:

FIG. 13 is a schematic drawing in section showing an intraosseous device inserted into bone marrow of a patient along with another example of a strap and supporting structure which may be carried in a kit in accordance with teachings of the present disclosure;

FIG. 14 is a schematic drawing in section showing another example of a strap and supporting structure which may be satisfactorily used to position an intraosseous device at a selected insertion site;

FIG. 15 is a schematic drawing in section with portions broken away of the strap and supporting structure of FIG. 14;

FIG. 16 is a schematic drawing showing an isometric view with portions broken away of the strap and supporting structure of FIGS. 14 and 15 releasably attached to the leg of a patient proximate the tibia;

DETAILED DESCRIPTION

Figure 1A:
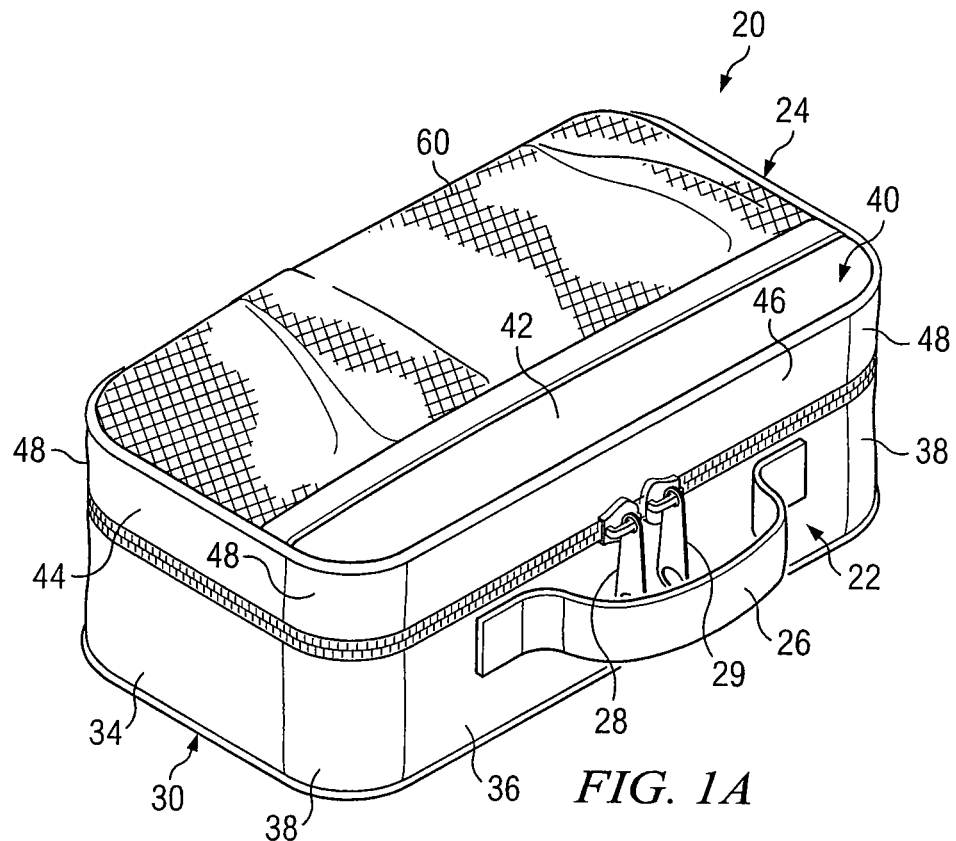
FIG. 1A is a schematic drawing showing an isometric view of one example of a kit which may be used to obtain access to a patient's vascular system in a first, closed position.

Preferred embodiments and associated features and benefits may be understood by reference to FIGS. 1A through 19 wherein like reference numbers indicate like features.

Vascular system access is essential for the treatment of many serious diseases and conditions and almost every serious emergency. Yet, many patients experience extreme difficulty obtaining timely treatment because of the inability to obtain or maintain venous access. The intraosseous (IO) space provides a direct conduit to systemic circulation and, therefore, is an attractive route to administer intravenous (IV) drugs and fluids. Rapid IO access offers great promise for almost any serious emergency that requires IV access to administer life saving drugs or fluids when traditional IV access is difficult or impossible.

IO access may be used as a "bridge" (temporary fluid and drug therapy) during emergency conditions until conventional IV sites can be found and utilized. This often occurs because fluids and/or medication provided via an IO access may stabilize a patient and expand veins and other portions of a patient's vascular system. Kits with IO devices and associated procedures incorporating teachings of the present disclosure may become the standard of care for administering medications and fluids in situations when IV access is difficult or not possible.

IO access generally provides rapid and reliable vascular access to administer life saving drugs or fluids, when traditional IV access is difficult or impossible. Such emergencies include shock, trauma, cardiac arrest, drug overdoses, diabetic coma, burns, dehydration, seizures, allergic reactions, and arrhythmias. There are more than 100 million visits to emergency rooms annually. Statistics show that vascular access may be difficult or impossible in 4 million patients annually.

Intraosseous access may be used as a "routine" procedure with chronic conditions which substantially reduce or eliminate the availability of conventional IV sites. Examples of such chronic conditions may include, but are not limited to, dialysis patients, seriously ill patients in intensive care units and epilepsy patients. Kits and intraosseous devices incorporating teachings of the present disclosure may be quickly and safely used to provide IO access to a patient's vascular system in difficult cases such as status epilepticus to give medical personnel an opportunity to administer crucial medications and/or fluids. Further examples of such acute and chronic conditions are listed near the end of this written description.

The term "driver" may be used in this application to include any type of powered driver or manual driver satisfactory for inserting an intraosseous device such as a penetrator assembly or IO needle into selected portions of a patient's vascular system. Various techniques may be satisfactorily used to releasably engage or attach an IO device and/or penetrator assembly with manual drivers and powered drivers. Various features and benefits of the present disclosure may be described with respect to kit having a driver to insert an intraosseous (IO) device into bone marrow of a patient at a selected insertion site. However, a kit with devices and components incorporating teachings of the present disclosure may be satisfactorily used to access various portions of a patient's vascular system. The present disclosure is not limited to IO devices and procedures.

The term "kit" may be used in this application to describe a wide variety of bags, containers, carrying cases and other portable enclosures which may be used to carry and store intraosseous devices and/or intravenous devices along with related components and accessories. Such kits and their contents along with applicable procedures may be used to provide access to a patient's vascular system in accordance with teachings of the present disclosure.

The present disclosure includes a wide variety of kits, devices and associated components which may be used to obtain vascular access to a patient. In some embodiments, such kits may include apparatus operable to access a patient's bone marrow using a driver, an intraosseous needle and one or more connectors to communicate fluids with the patient's bone marrow. Such kits may also include apparatus which allows monitoring a patient.

Kits incorporating teachings of the present disclosure may be rigid, semi-rigid or soft-sided. Such kits may provide a convenient way to carry various components and devices operable to achieve vascular access in an organized and systematic fashion. Such kits may present EMS first responders and other medical personnel with a well organized collection of components and devices to achieve vascular access by placement of peripheral intravenous (IV) catheters and/or intraosseous (IO) catheters. For some embodiments, a kit incorporating teachings of the present disclosure may be combination an IV kit, an IO kit and/or a unit dose kit in one convenient bag. Examples of various types of devices and components which may be carried in a kit in accordance with teachings of the present disclosure are shown in FIGS. 7A-19.

Securing devices incorporating teachings of the present disclosure may be provided in kits to allow easy removal and replacement of associated drivers. Such securing devices may include a wide variety of cradles and other types of holders with relatively rugged snap-in features to prevent undesired release of a driver from an associated securing device. Securing devices may be formed from plastic and/or glass composite materials to provide durability for repeated replacement and use of an associated driver. Such securing devices may releasably hold an associated driver in place within a kit so that the driver does not interfere with other devices and components disposed in the kit. A securing device may be positioned in a kit to clearly present an associated driver to a user during consideration of alternate vascular access routes.

Securing devices incorporating teachings of the present disclosure may make it easy for a user to extract an associated driver from a kit using only one hand. Other components such as penetrator assemblies and IO needles may be conveniently located in the kit to further minimize time and manipulations required for a user to attach an IO needle and insert the IO needle at a desired site in a patient. Such securing devices may also provide an easy site to return the driver to the kit after use. The associated driver may snap into place to securely protect the driver against accidental deployment until required for use in providing another IO access.

Kits incorporating teachings of the present disclosure may be used in locations where ruggedness and durability are of paramount importance. Such kits may be washable, water proof, temperature resistant, and/or crush proof. Such kits may have a wide variety of different shapes and colors. Kits incorporating teachings of the present disclosure may be any size as required to contain selected IO devices and IV devices which may be used to obtain vascular access. In some embodiment kits may be approximately ten inches in length by six to eight inches in width.

For some applications kits incorporating teachings of the present disclosure may be designed for use in military applications. Such kit may be as compact as feasible with components disposed in one or more compartments as necessary for an efficient use of space. Such kits may also include a manual intraosseous driver and related intraosseous components to access a patient's vascular system. Such kits may include intraosseous catheters, intravenous catheters, containers with sterile normal saline, tourniquets and IO/IV securing devices. Various components may be configured for particular branches of the military, e.g., Army, Navy, Air Force, Coast Guard and Special Forces.

Another benefit of the present disclosure may include forming a kit with one or more dividers having components and devices arranged in order on page one and page two corresponding with steps of a procedure such as treating a patient with an emergency condition or treating a patient for a chronic condition. The pages in a kit may be arranged to accommodate a wide variety of procedures. For example, if a kit will be used in an oncology related application or for treatment of other chronic conditions, the "pages" in the kit may be arranged based on the steps required to provide access to a patient's vascular system and to carry out a planned treatment.

Various techniques and procedures may be used to position and securely engage a supporting structure for an IO device at an insertion site. For some applications, various types of straps may be used. See FIGS. 8 and 11-17. Alternatively, various types of medical grade tape and adhesive materials (not expressly shown) may be used. Also, Velcro strips may be used (see FIGS. 15 and 16).

Figure 6:
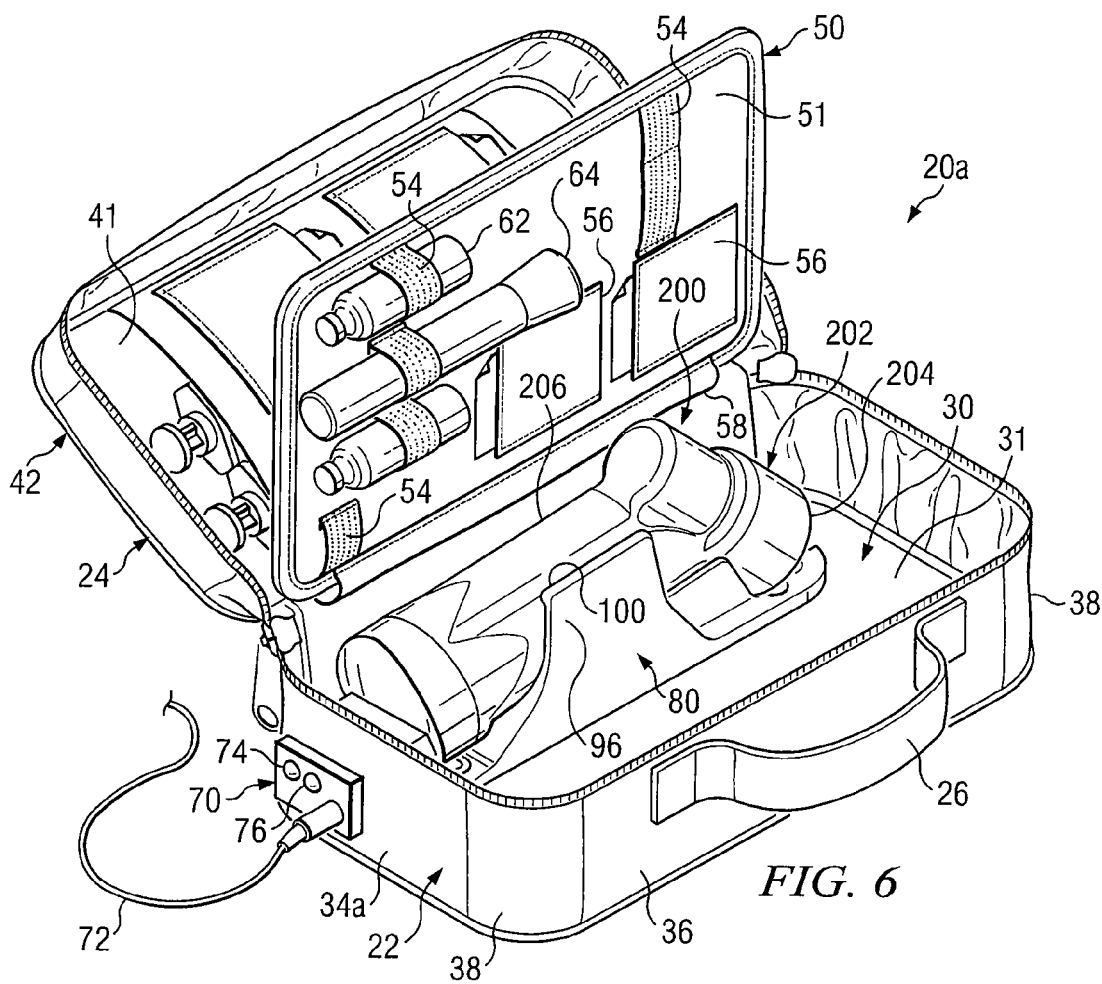
FIG. 6 is a schematic drawing showing an isometric view of one example of a kit in a second, open position with a powered driver installed in a securing device operable to recharge a battery carried within the powered driver in accordance with teachings of the present disclosure.
Figure 7A:
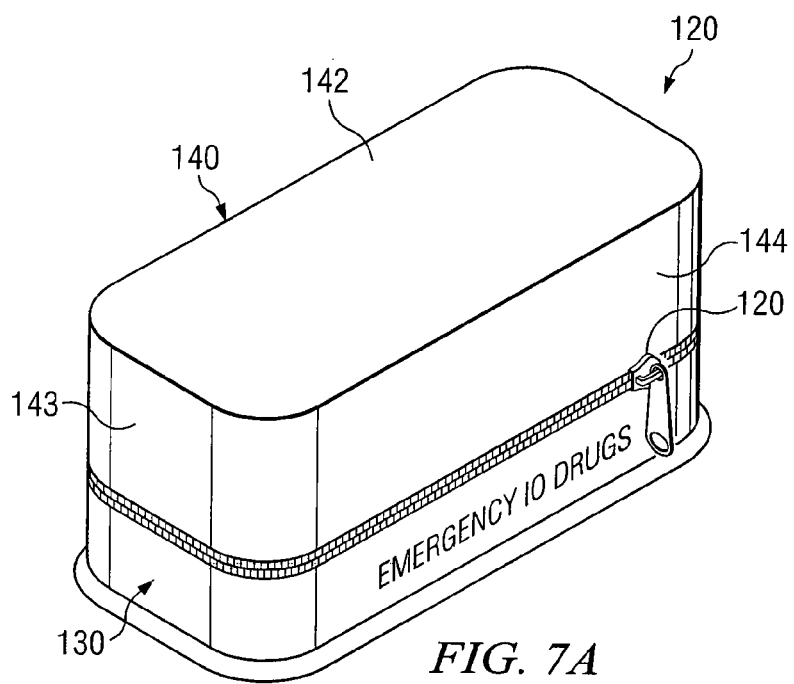
FIG. 7A is a schematic drawing showing another example of a kit in a first, closed position incorporating teachings of the present disclosure.
Figure 7B:
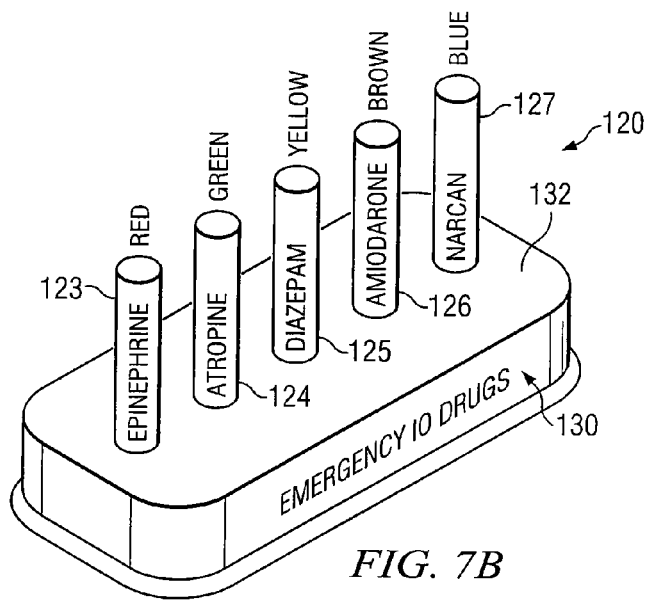
FIG. 7B is a schematic drawing showing an isometric view of the kit of FIG. 7A in a second, open position.

Some features and benefits of the present disclosure may be described with respect to kit 20 (See FIGS. 1A, 1B, 2) and kit 20a (See FIG. 6) and kit 120 (See FIGS. 7A and 7B). However, the present disclosure is not limited to kits with designs, features and/or contents as shown in FIGS. 1A-19.

For some applications kits 20, 20a and/or 120 may be semi-rigid or soft sided. Kits 20, 20a and 120 may be formed from a wide variety of materials including, but not limited to, nylon, cordura type materials, various types of polymeric and plastic materials. For some applications kits 20, 20a and/or 120 may be formed from relatively soft materials such as canvas, polyesters and similar materials. For other applications kits incorporating teachings of the present disclosure may be relatively rigid and formed from materials such as lightweight aluminum alloys and similar hard materials.

For embodiments such as shown in FIGS. 1A-2A and 6 kits 20 and 20a may be formed using compression molded techniques. For other applications, kits 20 and 20a may be formed with a foam liner having desired configuration and dimensions with an outer layer of sewn fabric. Such foam liners may be designed to protect the contents carried in the resulting kit from being damaged or crushed. Other alternative low-cost and reliable manufacturing techniques may be satisfactorily used to form kits in accordance with teachings of the present disclosure.

For some applications, kits 20 or 20a may be generally described as a two part molded case formed at least in part by compression molding ethylene vinyl acetate (EVA) foam. EVA may be generally described as a polymeric material with some of the characteristics of elastomeric materials and some characteristics of thermal plastic materials. However kits incorporating teachings of the present disclosure may be formed from a wide variety of polymeric materials, elastomeric materials and/or thermoplastic materials.

Kits 20 and/or 20a may have a nominal wall thickness of approximately 0.19 inches. Exterior surfaces of kits 20 and/or 20a may be covered by a durable layer of heavy dinear polyester or other suitable material. Interior portions of kits 20 and/or 20a may be formed in part by relatively smooth layers of urethane or relatively smooth layers of polyvinyl chloride (PVC). Such materials allow interior portions of kits 20 and/or 20a to be more easily cleaned, particularly after use during an emergency at a field location.

Kits 20 and/or 20a may have two segments or enclosures 22 and 24 with generally hollow, rectangular configurations and compatible dimensions. As a result first segment 22 and second segment 24 may be releasably engaged with each other to form an enclosure having desired dimensions and configurations to efficiently carry IO and IV devices and components associated with kits 20 and 20a. For some applications, first segment 22 and second segment 24 may have approximately the same dimensions and configurations such that each segment 22 and 24 may form approximately one-half of the resulting kit. For applications such as shown in FIGS. 1A-2A and 6, first segment 22 may have a greater height or depth as compared with second segment 24. Interior portions of first segment 22 may be sized to contain intravenous fluid bags, intravenous tubing and extension tubing, various types of connectors, syringes and Lidocaine or other anesthetizing agents.

For purposes of describing various features of the present disclosure, first segment 22 may be described as having generally rectangular bottom layer or base 30 with respective pairs of walls 34 and 36 extending therefrom. Base 30 may also include first surface or interior surface 31 (See FIGS. 2A and 6) and a second, exterior surface (not expressly shown). One wall 34a of kit 20a may be modified as compared to corresponding wall 34 of kit 20. Wall 34a will be discussed later in more detail. Generally rounded corners 38 may be formed between adjacent walls 34 and 36.

Second segment 24 may be defined in part by top layer or cover 40. Sometimes top layer 40 may also be referred to as a lid. Top layer 40 may include first surface or interior surface 41 (See FIGS. 2A and 6) and second surface or exterior surface 42 (See FIG. 1A). Respective pairs of walls 44 and 46 may extend from top layer 40. Respective rounded corners 48 may be formed between adjacent walls 44 and 46.

For some applications, a pair of zippers 28 and 29 may be used to releasably engage second segment 24 with first segment 22 when associated kits 20 or 20a is in their respective first, closed position. (See FIG. 1A). For other applications a single zipper may be satisfactorily used. For some applications a fluid seal (not expressly shown) may be formed when the perimeter of first enclosure 22 is engaged with the perimeter of second enclosure 24 when kits 20 and/or 20a are in their first, closed position.

First segment 22 and second segment 24 may be hinged with each other along one side of respective kits 20 and 20a. Fabric type hinge 58 or other suitable low cost, reliable hinge mechanism may be used to allow movement of second segment 24 relative to first segment 22 to open and close the associated kit 20 or 20a. Handle 26 may be attached with exterior portion of kits 20 and 20a opposite from the hinge 58 located on interiors of kits 20 and 20a. Handle 26 may be formed from lightweight, durable web type material or any other suitable material.

Zippers 28 and 29 may be moved around the three edges of contact between first enclosure 22 and second enclosure 24 to engage and disengage adjacent portions of enclosures 22 and 24. Zippers 28 and 29 and associated zipper mechanisms may be formed from durable, rustproof material and extend along three edges of contact between first enclosure 22 and second enclosure 24.

After kits 20 and/or 20a have been used at a field location or at a medical facility, the used kit may be returned to a central location for cleaning and replacement of any missing components or devices. For some applications breakable seal 23 (See FIG. 1B) may be engaged with zippers 28 and 29 to indicate that the associated kit 20 or 20a has been cleaned, inspected, any missing components or devices replaced and is now ready to be used to provide access to a patient's vascular system.

One or more panels or dividers may be disposed within kits incorporating teachings of the present disclosure. The dividers may also be referred to as "boards." For embodiments represented by kits 20 and 20a one edge of each divider 50 may be engaged with associated hinge 58 to allow rotating movement of each divider 50 relative to hinge 58 when associated kit 20 or 20a is in its first, open position.

Dividers 50 may be formed from polyvinyl chloride (PVC) or other suitable materials. Each divider 50 may have a generally rectangular configuration with dimensions compatible with nesting each divider within segments 22 and 24 when associated kit 20 or 20a is in its first, closed position. For some applications dividers 50 may be about 0.050 to 0.060 inches thick. The width and other characteristics of hinge 58 may also be selected to accommodate nesting of each divider 50 within segments 22 and 24 when associated kit 20 or 20a is in its first, closed position.

Figure 2A:
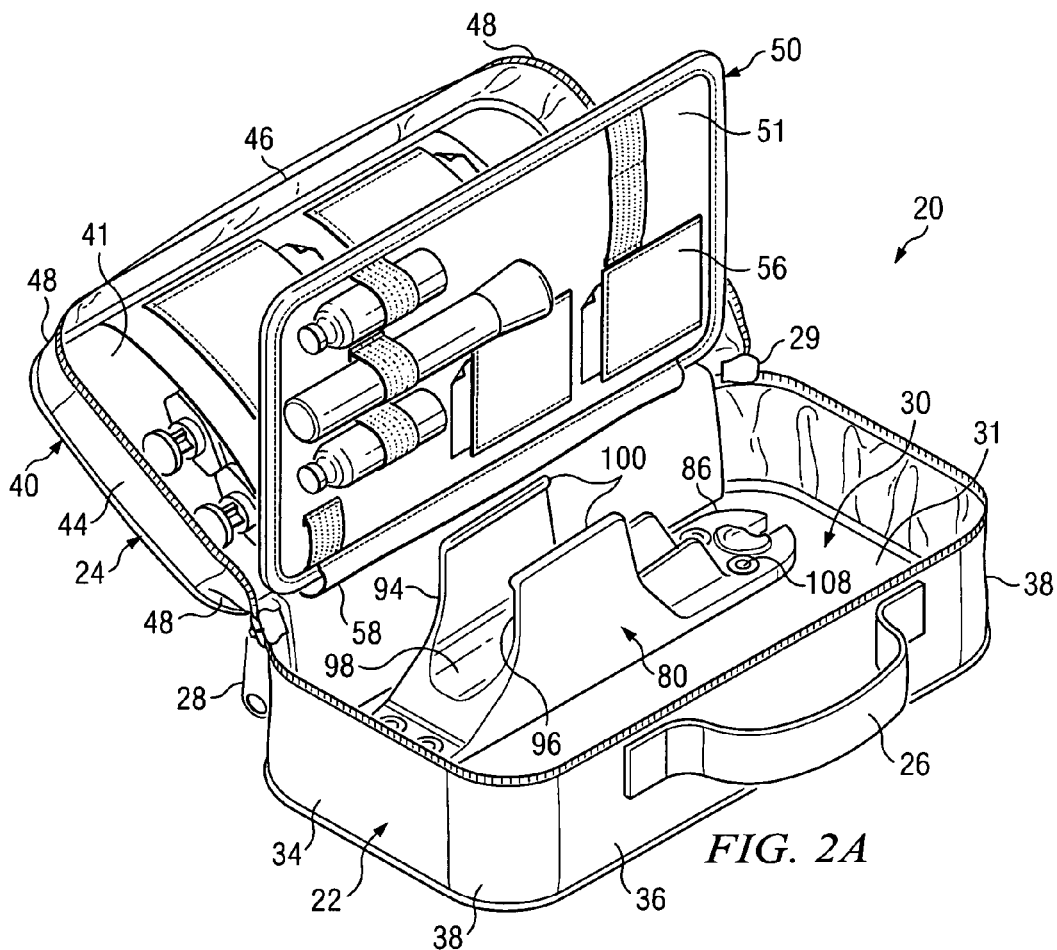
FIG. 2A is a schematic drawing showing an isometric view of the kit in FIG. 1A in an open position along with examples of intraosseous and intravenous devices and components disposed therein.
Figure 2B:
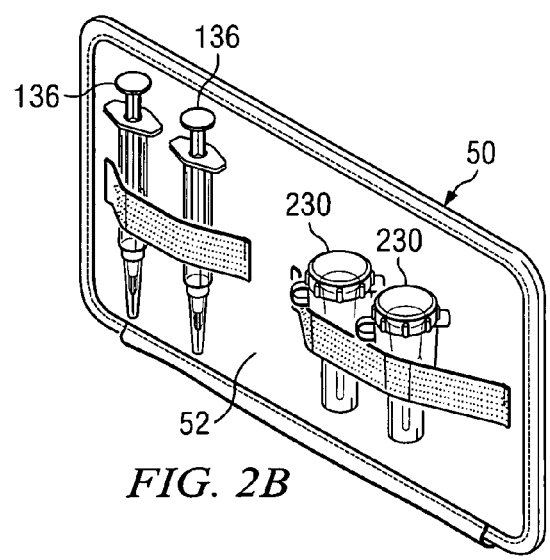
FIG. 2B is a schematic drawing showing one side of a divider or panel which may be disposed in the kit of FIG. 2A along with examples of intraosseous and intravenous devices and components attached thereto.

Each divider 50 may also include first surface 51 and a second surface 52. Surfaces 51 and 52 may sometimes be referred to as "pages." For embodiments such as shown in FIGS. 2A, 2B and 6, first surface 51 or page 1 and second surface 52 or page 2 may include a plurality of holders such as elastic straps or bands 54 and pockets 56. Velcro type straps, holders and elastic bands may also be used.

For example, "page one" or first surface 51 of divider 50 may present EMS personnel with devices, components and instructions used to select and clean a site for vascular access. Such components and devices may include containers 62 with cleaning fluids, alcohol wipes or other prep materials, flashlight 64 and a tourniquet (not expressly shown). Written instructions for selecting an insertion site and/or locating a vein may be provided in pockets 56 on page one.

"Page Two" or second surface 52 of divider 50 may include devices and components that allow EMS personnel to access a patient's vascular system via a peripheral vein or an intraosseous route. Such components may include intravenous catheters, intraosseous needles and other components that may be used to access a patient's vascular system. As shown in FIG. 2B, one or more containers 230 with respective IO devices disposed therein may be releasably engaged with second surface 52 or page two of divider 50. One or more IV devices such as IV needle sets 136 may also be releasably engaged with second surface 52. Each IV needle set 136 may include a syringe, IV needle and cover for the IV needle.

For some applications, interior surface 41 of cover 40 may also function as page three with additional devices, components and instructions attached thereto. For example, when kits 20 and/or 21a are used in an emergency environment to provide IO access to a patient, interior surface 41 or page three may include devices and components used to secure and intraosseous device and/or an IV device at the insertion site and to further prepare the patient for movement to an EMS treatment facility. Components and devices such as tape, dressing materials, an arm-board or splint and other components operable to secure a catheter or an intraosseous line may be provided on page three. Various types of straps and supporting structures for IO devices may be releasably attached to page three or interior surface 41. See some examples in FIGS. 8-17.

Outside pocket 60 formed from mesh type material may be attached to exterior surface 42 of cover 40. Outside pocket 60 may hold printed reference materials such as quick reference cards. For some applications elastic cords (not expressly shown) may also be provided on exterior portion of kits 20 and 20a to hold such materials.

Velcro or elastic strips or loops or any other fastening device may be used to position components on dividers 50. In lieu of dividers 50, IO and IV devices and related components may be configured in some other arrangement or organizing mechanism such as compartments or smaller containers carried in a kit.

A device for accessing an intraosseous space such as a powered driver (See FIG. 4) or a manual driver (See FIGS. 18 and 19) may be carried in first segment 22. For some applications a securing device such as shown in FIGS. 2A, 3, 5 and 6 may be disposed within first segment 22 to releasably hold a driver. For other applications a powered driver and/or manual driver may be placed in a collapsible bag or pouch and placed within first segment 22 or other portions of kit 20 and/or 20a. For still other applications a powered driver and/or manual driver may be carried in a bag or pouch attached to exterior portions (not expressly shown) of kit 20 and/or 20a.

Powered driver 200 may include housing 202 with various types of motors and/or gear assemblies disposed therein (not expressly shown). A rotatable shaft (not expressly shown) may be disposed within housing 202 and connected with a gear assembly. Various types of fittings and/or connectors may be disposed proximate one end of the rotatable shaft extending from end 204 of housing 202. For some applications a pin type fitting or connector such as drive shaft 216 may be used. A matching box type fitting or connector receptacle may be provided on an intraosseous device such that power driver 200 may be releasably engaged with the intraosseous device. For some applications, drive shaft 216 may have a pentagonal shaped cross section with tapered surfaces formed on the exterior thereof. Fittings and/or connections with various dimensions and configurations may be satisfactorily used to releasably engage an intraosseous device with a powered driver.

Figure 18A:
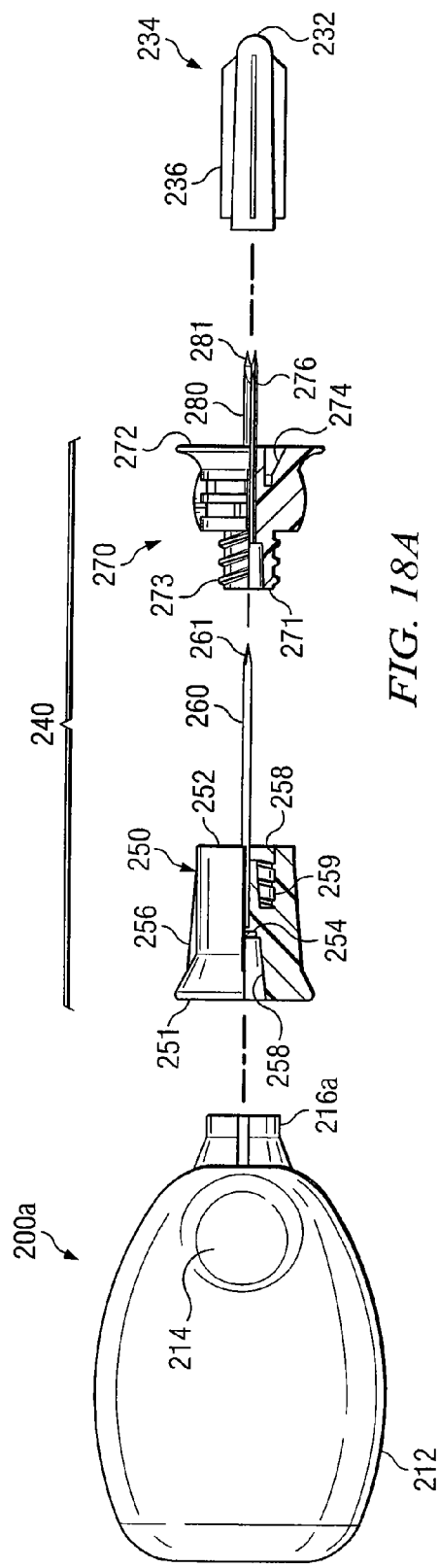
FIG. 18A is a schematic drawing showing an exploded view of a manual driver and associated intraosseous device which may be carried in a kit in accordance with teachings of the present disclosure.
Figure 18B:
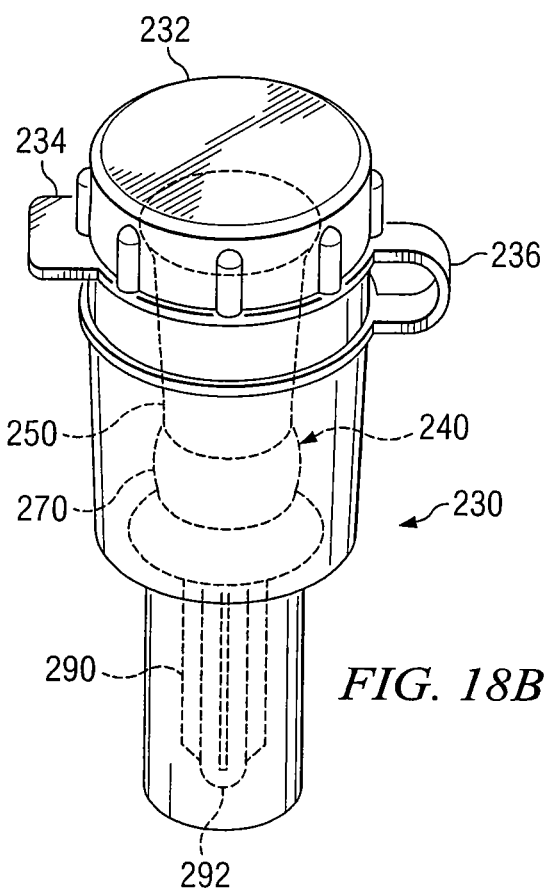
FIG. 18B is a schematic drawing showing an isometric view of a container with one example of an intraosseous device disposed therein.

Container 230 as shown in FIGS. 2B and 18B may include lid 232 along with associated tab 234. Tab 234 may be configured to be flipped open with one or more digits of an operator's hand. With lid 232 open, an operator may releasably engage a driver with an IO device disposed in container 230. For example, drive shaft 216 of powered driver 200 may be releasably engaged with box type connector or receptacle 258 of penetrator assembly 240. See FIGS. 4 AND 18A. Flexible strap 236 may be used to retain lid 232 with container 230 after lid 232 has been opened.

Handle 206 may include a battery (not expressly shown) or other power source. Handle 206 may also include trigger assembly 208 for use in activating powered driver 200. Examples of powered drivers are shown in pending patent application Ser. No. 10/449,503 filed May 30, 2003 entitled Apparatus and Method to Provide Emergency Access To Bone Marrow, Ser. No. 10/449,476 filed May 30, 2003 entitled Apparatus and Method to Access Bone Marrow and Ser. No. 11/042,912 filed Jan. 25, 2005 entitled Manual Interosseous Device.

Various types of intraosseous devices, intraosseous needles and/or penetrator assemblies may be carried in a kit incorporating teachings of the present disclosure. See for example FIG. 2B. Intraosseous devices 160 and 160a which are shown in FIGS. 8, 11, 12 and 13 may be carried in a kit along with powered driver 200 and inserted into a patient's bone marrow in accordance with teachings of the present disclosure.

For some applications a securing device designed to accommodate one or more specific types of drivers may be disposed within first segment 22. For other applications more generic types of holders or cradles may be placed within first segment 22. For embodiments such as shown in FIGS. 2A, 3, 5 AND 6 securing device or cradle 80 may be designed to accommodate powered drivers such as powered driver 200. Cradles and holders incorporating teachings of the present disclosure may be fabricated from a wide variety of thermoplastic and/or polymeric materials filled with glass fibers.

Length 82 and width 84 of cradle 80 may be selected to be compatible with interior dimensions of first enclosure 22 and similar dimensions associated with a driver that will be releasably engaged with cradle 80. For some applications first end 86 and second end 88 may have generally rounded configurations. Notch 90 may be formed in first end 86 to accommodate drive shaft 216 extending from end 204 of power driver 200.

First longitudinal edge 91 and second longitudinal edge 92 may be spaced from each other and extend generally parallel with each other between first end 86 and second end 88. For some applications, ends 86, 88 and longitudinal edges 91, 92 may fit flush with interior surface 31 of bottom layer 30. Maintaining close contact between interior surface 31 and adjacent portions of cradle 80 may substantially reduce or minimize problems associated with cleaning an associated kit after use, particularly after used during an emergency at a field location.

Various types of holders, clamps and/or quick release mechanisms may be provided on a cradle incorporating teachings of the present disclosure. For embodiments represented by cradle 80 a pair of arms 94 and 96 may project from respective longitudinal edges 91 and 92. Arms 94 and 96 may be relatively strong with sufficient flexibility to allow inserting and removing portions driver 200 from engagement with cradle 80. The height of arms 94 and 96 relative to longitudinal edges 91 and 92 may be based at least in part on the height or depth of first enclosure 22 and corresponding dimensions of driver 200. Support surface 98 may be disposed between arms 94 and 96 in an elevated position relative to longitudinal edges 91 and 92. The location of support surface 98 may be selected to accommodate corresponding dimensions of driver 200 and particularly handle 206.

The spacing or gap formed between first arm 94 and second arm 96 may be selected to accommodate the width of handle 206 of driver 200. Respective ribs 100 may be formed approximate the end of each arm 94 and 96 opposite from longitudinal edges 91 and 92. Ribs 100 preferably extend inwardly relative to associated arm 94 and 96. The dimensions of arms 94 and 96, the gap formed therebetween, and associated ribs 100 may be selected to be compatible with forming a snug but releasable snap type fit with adjacent portions of handle 206 of driver 200.

Figure 3:
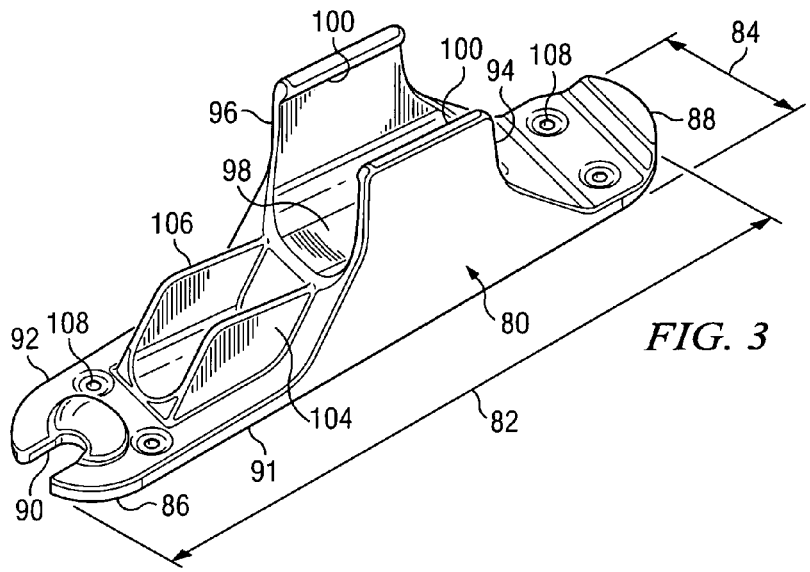
FIG. 3 is a schematic drawing showing an isometric view of one example of a securing device which may be installed in a kit to releasably hold a drive in accordance with teachings of the present disclosure.
Figure 4:
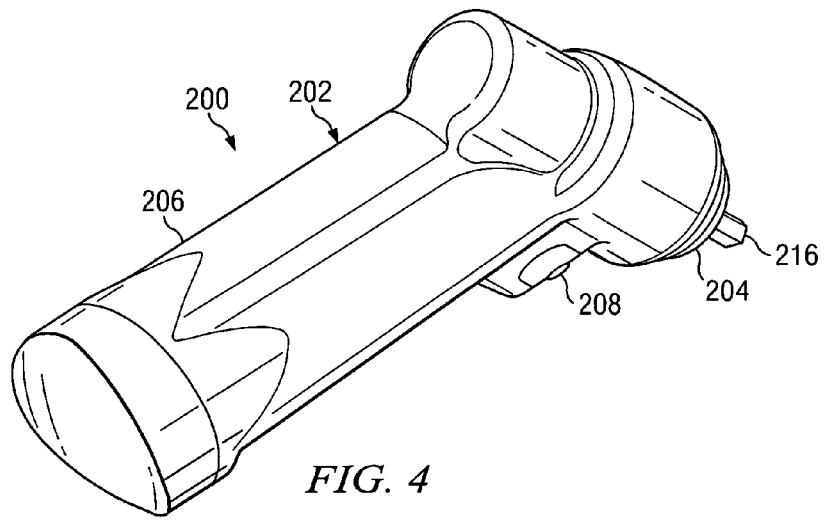
FIG. 4 is a schematic drawing showing one example of a powered driver and penetrator assembly which may be included in a kit in accordance with teachings of the present disclosure.
Figure 5:
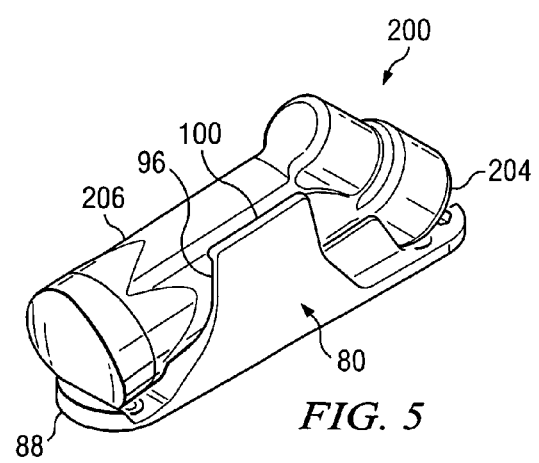
FIG. 5 is a schematic drawing showing an isometric view of one example of a powered driver and securing device releasably engaged with each other in accordance with teachings of the present disclosure.

For some applications first wall 104 and second wall 106 may be disposed between first end 86 and supporting surface 98 such as shown in FIG. 3. The spacing between first wall 104 and second wall 106 may be selected to correspond with corresponding dimensions of handle 206 of driver 200 and particularly dimensions associated with trigger assembly 208. Walls 104 and 106 may cooperate with each other to provide a "trigger guard" to prevent accidental activation of driver 200 when kit 20 and/or 20*a* are in their first, closed position.

One or more holes 108 may be formed in cradle 80 approximate first end 86 and second end 88. Holes 108 may be sized to receive various types of fasteners such as rivets and/or screws (not expressly shown). Such fasteners may be used to secure cradle 80 at a desired location within first enclosure 22.

Materials used to form cradle 80 may be relatively low cost but must also have sufficient durability for repeated insertion and removal of an associated driver. For some applications arms 94 and 96 may be designed to allow insertion and removal of an associated driver at least five hundred times. Arms 94 and 96 may also have sufficient stiffness and strength to allow associated driver 200 to snap into place. The stiffness of arms 94 and 96 may be selected such that driver 200 will not be inadvertently released from cradle 80 if kit 20 or 20*a* should be dropped or otherwise mishandled.

For embodiments such as shown in FIG. 6, second end 88 (not expressly shown) of cradle 80*a* may be modified to include electrical contacts used to charge a battery or other power source disposed in handle 206 of driver 200. Electrical connector assembly 70 may be disposed on exterior portions of wall 34*a* to accommodate inserting charging cable 72 extending from an appropriate charger (not expressly shown). Lights 74 and 76 may be provided as part of electrical connector assembly 70 to indicate the status of a battery or other power source disposed in handle 206 after each use of powered driver 200 and to indicate the status of recharging powered driver 200.

Various types of indicator lights may be used. For some applications light 74 may be yellow to indicate that a battery (not expressly shown) in power driver 200 needs to be recharged. Light 76 may be green to indicate that the charging is not required or that charging of associated powered driver 200 has been satisfactorily completed. For some applications, kit 20*a* will preferably be in its first, open position during charging of powered driver 200.

Prehospital and combat situations are often ideally suited to use "unit dose" containers of various types of medications. Emergency medical personnel often need only a one-time dose of medication, such as an antidote for poison or epinephrine to stabilize the patient. Unit dose ampules are widely used by paramedics to give a predetermined amount of medication for a particular indication. A limited number of drugs may satisfactorily fill such needs.

Kit 120 as shown in FIGS. 7A and 7B represents one example of a kit containing unit doses in accordance with teachings of the present disclosure. For some applications, kit 120 may be carried separate from previously discussed kits 20 and 20*a*. For other applications kit 120 may be disposed within kits 20 and/or 20*a*. Kit 120 is shown in FIG. 7B in its second, open position with cover 140 removed to provide access to ampules 123-127 containing respective unit doses of medication.

Figure 1B:
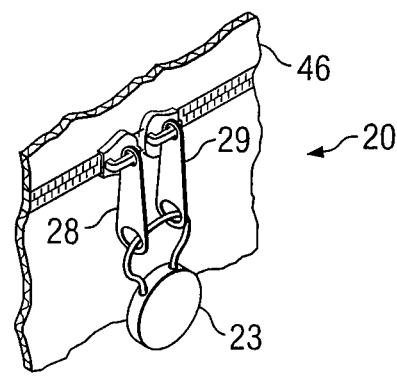
FIG. 1B is a schematic drawing with portions broken away showing one example of a breakable seal which may be used to indicate status of the kit of FIG. 1B.

Kit 120 may include base portion 130 and cover 140. Zipper 122 or other types of closures may be satisfactorily used to releasably engage cover 140 with base portion 130. For some applications a pair of zippers and a breakable seal such as shown in FIG. 1B may be used with kit 120. Kit 120 is shown in FIG. 7A in its first, closed position with cover 140 releasably engaged with base portion 130.

For embodiments such as shown in FIGS. 7A and 7B, kit 120 may be described as having a generally rectangular configuration with rounded corners. Cover 140 may be generally described as a hollow enclosure defined in part by top layer 142 with four (4) walls extending therefrom. Walls 143 and 144 are shown in FIG. 7A. Interior portions of cover 140 are preferably open to accommodate storage of ampules 123-127.

Base 130 may be formed from a relatively thick layer of material satisfactory for use. A plurality of holes may be formed in interior surface 132 of base 130 satisfactory to accommodate releasably storing each ampule 123-127 in a respective hole. The exterior configurations of base 130 may also be defined in part by walls and rounded corners which are preferably compatible with the walls and rounded corners associated with cover 140.

Base portion 130 as shown in FIG. 7B may function as a rack releasably holding a plurality of single use (unit dose) ampules which may meet many (if not most) of an emergency medical service provider's immediate needs. For example, ampule 123 may contain epinephrine for cardiac arrest and life threatening allergies. Ampule 124 may contain atropine for cardiac arrest and chemical exposures. Ampule 125 may contain diazepam for seizures and emergency sedation. Ampule 126 may contain amiodarone for cardiac arrhythmias. Ampule 127 may contain narcan for drug overdose. Each ampule 123-127 may be clearly labeled so that an appropriate drug may be quickly and accurately selected in an emergency. As shown in FIGS. 7A and 7B, kit 120 may contain medications in an easy to carry and maintain rack or stand such as base 130. Kit 120 may include zip lock cover 140 which is easy to remove in an emergency.

The ability to satisfactorily insert an IO device such as an IO needle at a desired insertion site may be problematic when a patient is moving or has the potential to move. Inserting an IO device in the wrong place may expose a patient to potential harm. Patient movement may be of special concern for patients suffering from status epilepticus or violent patients (drug overdoses or mental status changes) that need to be controlled for their safety and treatment. Epileptic patients may shake violently for prolonged periods which makes starting a conventional IV nearly impossible. Likewise, it may be difficult to accurately place an IO device at a desired insertion site in these patients. Although target areas for successful IO placement such as a patient's tibia and humerus are often larger than target areas for placement of an IV device, problems with inserting an IO device at a desired insertion site may be minimized by using stabilization devices and supporting structures incorporating teachings of the present disclosure. Such devices and supporting structures may be easy to apply, even in difficult field environments.

FIGS. 8, 11, 12, 13, 14 and 17 show various examples of an intraosseous device inserted into a patient's bone marrow to provide vascular access in accordance with teachings of the present disclosure. Bone 152 and associated bone marrow 154, shown in FIGS. 8, 11, 12, 13, 14 and 17, may be representative of the tibia in a patient's leg. The upper tibia proximate a patient's knee may often be used as an insertion site for IO access to a patient's vascular system. A humerus may also be used as an insertion site for IO access to a patient's vascular system.

Figure 8:
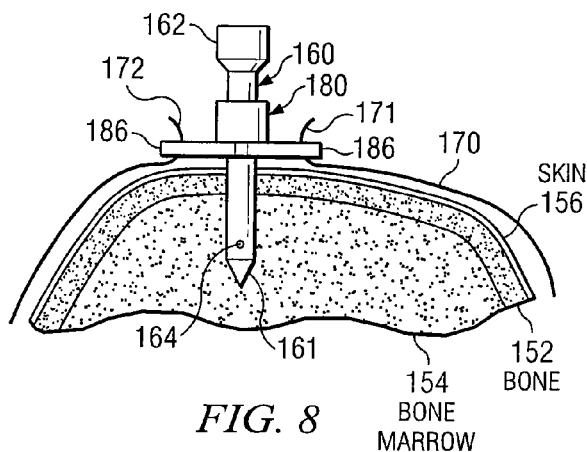
FIG. 8 is a schematic drawing in section showing an intraosseous device inserted into bone marrow of a patient after using various devices and components carried in a kit in accordance with the teachings of the present disclosure.

FIG. 8 shows one example of an intraosseous device which may have been inserted into a patient's bone marrow using a kit containing various devices and components in accordance with teachings of the present disclosure. For this example, intraosseous device 160 may be generally described as intraosseous (IO) needle 160 having a hollow, longitudinal bore extending therethrough (not expressly shown). IO devices 160 may be releasably attached to page 2 of kits 20 and/or 20*a*.

First end or tip 161 of IO needle 160 may be designed to drill or cut through bone 152 and penetrate associated bone marrow 154. Tip 161 may be open to allow communication of fluids with bone marrow 154. Also, one or more side ports 164 may be formed in IO needle 160 to allow communication of fluids therethrough. Second end 162 of IO needle 160 may have various types of connections including, but not limited to, a conventional Luer lock connection (not expressly shown) associated with supplying IV fluids and medications to a patient.

Figure 9:
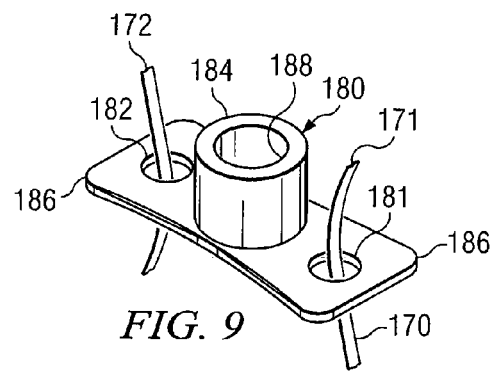
FIG. 9 is a schematic drawing in elevation with portions broken away showing one example of a strap and supporting structure which may be carried in a kit and used to position an intraosseous device at a selected insertion site.

Strap 170 and supporting structure 180 such as shown in FIGS. 8 and 9 may be carried in a kit in accordance with teachings of the present disclosure. Strap 170 may be formed from various types of elastomeric and/or nonelastomeric materials compatible with contacting skin 156 and other soft tissue covering a patient's bone at a selected insertion sight. The dimensions and configuration of strap 170 may be selected to form satisfactory engagement with adjacent portions of leg 150, an arm, or other desired sites for providing IO access to a patient's vascular system.

Strap 170 may include first end 171 and second end 172 sized to be inserted through holes 181 and 182 of supporting structure 180. Strap 170 and supporting structure 180 cooperate with each other to prevent accidental removal or withdrawal of IO needle 160 from an insertion site. Strap 170 and supporting structure 180 also cooperate with each other to prevent excessive movement or rocking of IO needle 160 relative to the insertion site.

Supporting structure 180 may include relatively short, hollow cylinder 184 with a pair of flanges or wings 186 extending therefrom. Holes 181 and 182 may respectively be formed in each wing or flange 186. Wings 186 may be formed from relatively flexible material which will conform with adjacent portions of a patient's skin, soft tissue and bone. Hollow cylinder 184 may be formed from relatively rigid material to prevent undesired movement of associated IO needle 160. Interior dimensions of hollow cylinder 184 may correspond approximately with the exterior dimensions of IO needle 160 to provide a relatively snug fit therebetween.

Figure 10:
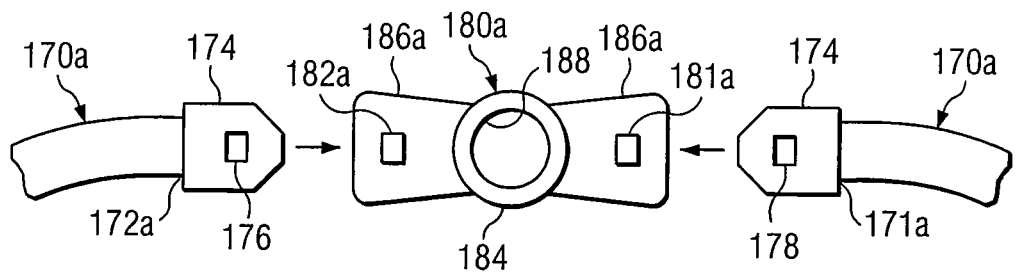
FIG. 10 is a schematic drawing showing a plan view with portions broken away of another example of a strap and supporting structure which may be carried in a kit and used to position an intraosseous device at a selected insertion site.

For embodiments such as shown in FIG. 10, supporting structure 180a may include wings or tabs 186a which have been modified to include respective projections 181a and 182a extending there from. Strap 170a may be modified as compared with strap 170 by attaching respective buckles 174 with first end 171a and second end 172a. Each buckle 174 may include respective hole 176 sized to receive associated projection 181a and 182a formed on tabs 186a.

Supporting structure 180a may be placed at an IO insertion site. Buckle 174a at first end 171a of strap 170a may be releasably engaged with corresponding projection 181a. Strap 170a may then be extended around patient's leg or other bone to allow engaging buckle 174a at second end 172a with associated projection 182a. For such applications, strap 170a may be formed from elastomeric material.

For some applications supporting structure 180 may be placed at an insertion site prior to installing IO device 160. IO device 160 may then be inserted through the longitudinal bore of supporting structure 180. For other applications an IO device with exterior dimensions and exterior configuration of the IO device may be compatible with interior dimensions 188 of supporting structure 180 may first be installed at a desired insertion site. Supporting structure 180 may then be fitted over the installed IO device (not expressly shown) by placing the IO device through the longitudinal bore of supporting structure 180. Strap 170a may then be engaged with respective projections 181 and 182.

Figure 11:
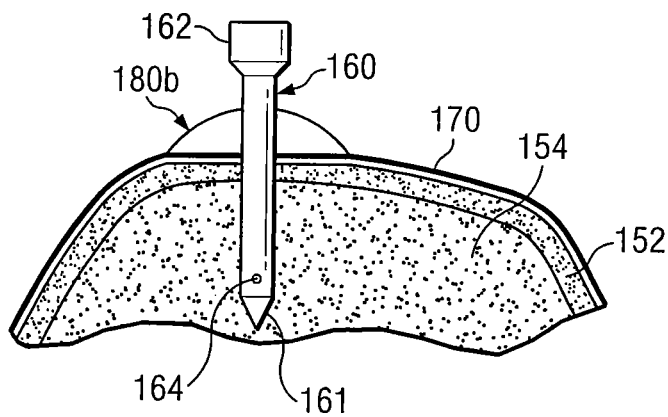
FIG. 11 is a schematic drawing in section and in elevation showing an intraosseous device inserted into bone marrow of a patient along with another example of a strap and supporting structure which may be carried in a kit in accordance with teachings of the present disclosure.

FIG. 11 shows IO needle 160 inserted into bone marrow 154. Supporting structure 180b may be used to stabilize IO needle 160 and limit excessive movement relative to bone 152. Supporting structure 180b may be generally described as having a domed shape configuration. The dimensions of supporting structure 180b may be selected to be compatible with a desired insertion site. A longitudinal bore or a longitudinal opening (not expressly shown) may extend through supporting structure 180b. The longitudinal bore may have dimensions compatible with exterior dimensions of IO needle 160. Supporting structure 180b may be formed from various types of semi-rigid silicone based materials and/or materials satisfactory for providing required support. A pair of holes (not expressly shown) may be provided in supporting structure 180b to accommodate the use of strap 170. However, other straps such as shown in FIGS. 10, 14 and 15 and/or adhesive materials (not expressly shown) may be satisfactory used to position supporting structure 180 at a desired insertion site.

Figure 12:
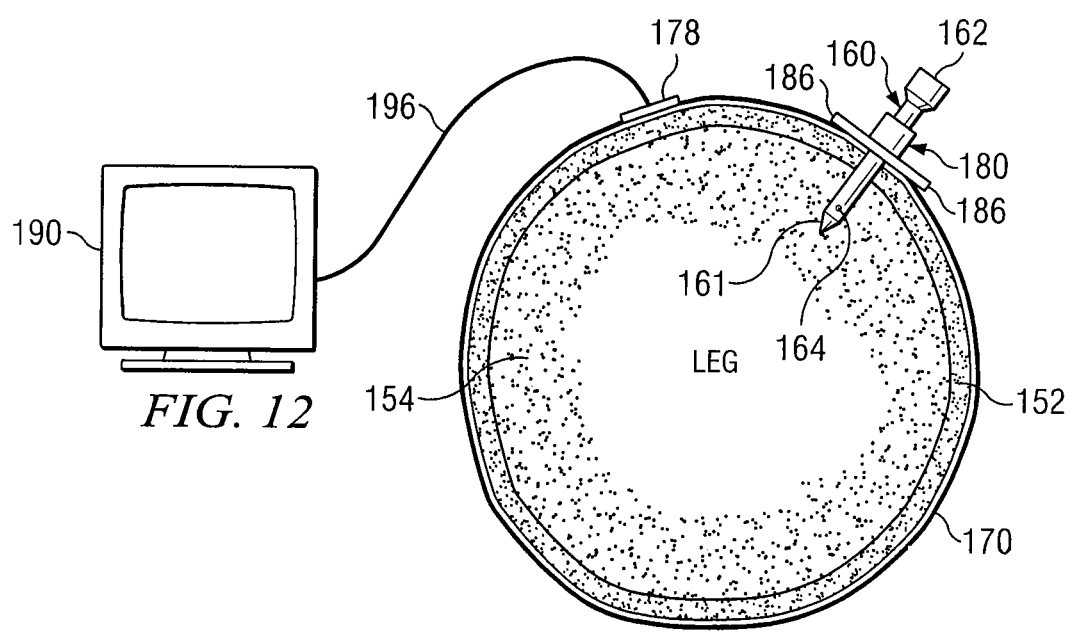
FIG. 12 is a schematic drawing in section showing an intraosseous device inserted into bone marrow of a patient along with another example of a strap and supporting structure which may be carried in a kit in accordance with teachings of the present disclosure.

FIG. 12 shows IO 160 inserted into bone 152 and associated bone marrow 154. Strap 170 may be placed around bone 152 and attached to supporting structure 180 as previously described. Sensor 178 may be attached to strap 170 for use in measuring various parameters associated with providing fluids and/or medications through IO device 160 to bone marrow 154. Such parameters may include, but are not limited to, pressure and/or changes in the size of a patient's leg, temperature and/or pulse rate. When sensor 178 detects a preset value for one or more of these parameters, an alarm may be sounded. For some applications sensor 178 may be coupled with monitor 190 and/or a general purpose computer (not expressly shown). The general purpose computer may include one or more programs operable to stop infusion of fluids and/or medication through associated IO device 160 in the event one or more parameters exceeds preset limits.

FIG. 13 shows IO device 160a inserted into bone 152 and associated bone marrow 154. IO device 160a may be equipped with pressure transducer 192 proximate tip 161 to measure intraosseous pressure. For some applications, a similar needle (not expressly shown) may be placed in a leg muscle to measure intra-compartment pressure.

Seal assembly 195 may be used to isolate transducer wire 196 so that infusions of fluids may proceed while, at the same time, measuring intravenous pressure at tip 161. Measurements from sensor 192 may be analyzed by a computer (not expressly shown) to manage changes in a patient's condition by initiating pre-set increases in infusion pressure, controlling the rate of infusion or stopping infusion all together and alarming the patient and/or medical personnel if pressure limits are exceeded.

FIGS. 14, 15 and 16 show one example of a supporting structure or guide which may be disposed at a desired insertion site such as the upper tibia proximate a patient's knee. Supporting structure or guide 180c may be generally described as having a dome shaped configuration with cavity or recess 194 formed therein and sized to receive an intraosseous device. For example, recess 194 may be sized to accommodate an intraosseous device such as penetrator assembly 240. See for example FIG. 17.

Supporting structure or guide 180c may be formed from various polymeric and/or thermoplastic materials having desired rigidity and strength to direct insertion of an intraosseous device at a desired insertion site. Supporting structure 180c may also be formed from various types of elastomeric and/or nonelastomeric materials satisfactory for use in forming a guide or supporting structure to direct insertion of an intraosseous device at a desired insertion site.

For some applications strap 170c may include one or more strips of hook and loop type material 198 (sometimes referred to as Velcro® strips) disposed proximate first end 171c and second end 172c of strap 170c. The configuration, size and dimensions of Velcro® strips 198 may be modified to allow strap 170c to releasably attach supporting structure 180c with a leg or other portions of a patient's body having various dimensions. For some applications supporting structure 180c may include target 199 disposed within recess 194 for use by an operator to more precisely direct insertion of an associated IO device at a desired insertion site.

Figure 17:
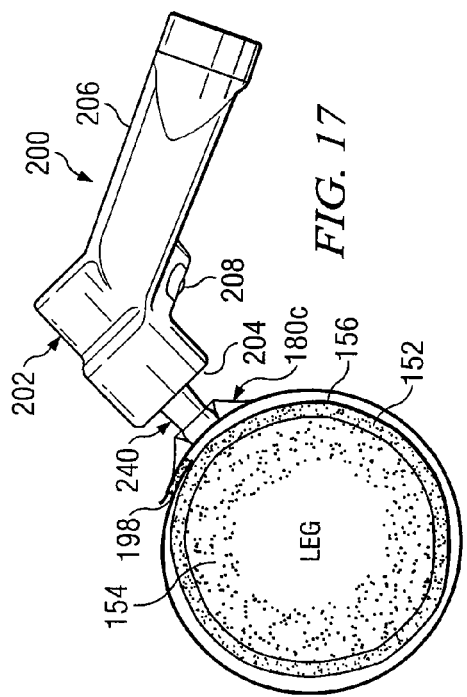
FIG. 17 is a schematic drawing showing another example of a powered driver which may be carried in a kit incorporating teachings of the present disclosure along with a strap and supporting structure for an associated intraosseous device.

FIG. 17 shows powered driver 200 being used to insert penetrator assembly 240 at an insertion site identified by guide or supporting structure 180c. Powered driver 200 may be further stabilized with various types of straps and/or medical grade tape (not expressly shown) prior to inserting penetrator assembly 240.

Figure 19:
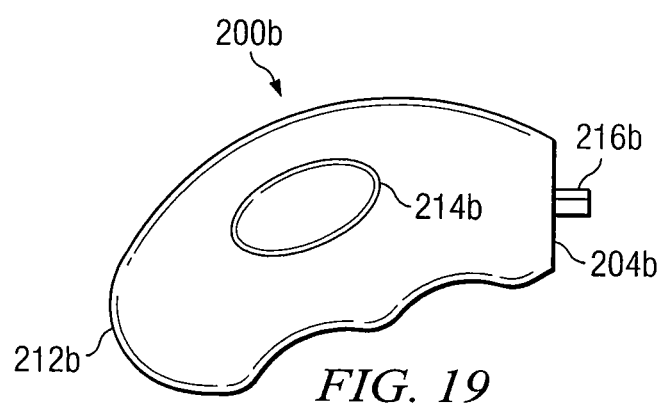
FIG. 19 is a schematic drawing showing another example of a manual driver which may be carried in a kit in accordance with teachings of the present disclosure.

FIGS. 18A and 19 show examples of manual drivers which may be carried in a kit in accordance with teachings of the present disclosure. For some applications, a kit may contain only a powered driver or only a manual driver. For other applications, a kit incorporating teachings of the present disclosure may include both a powered driver and a manual driver. Examples of manual drivers are shown in pending patent application Ser. No. 10/449,503 filed May 30, 2003 entitled Apparatus and Method to Provide Emergency Access To Bone Marrow and Ser. No. 11/042,912 filed Jan. 25, 2005 entitled Manual Interosseous Device.

Manual driver 200a may include handle 212 with drive shaft 216 extending therefrom. Manual driver 200a may also include an optional ratchet mechanism (not expressly shown). Handle 212 may be formed in a variety of shapes, such as with finger grips 214. Handle 212 may be formed from materials satisfactory for multiple uses or may be formed from materials satisfactory for one time or disposable use. Handle 212 may have an ergonomically designed shape suitable for grasping with a hand and/or fingers during manual insertion of an IO device into bone and associated bone marrow.

FIG. 18A shows an exploded view of manual driver 200a and penetrator assembly 240. Penetrator assembly 240 may include an outer penetrator such as a cannula, hollow tube or hollow drill bit and an inner penetrator such as a stylet or trocar. Various types of outer penetrators may be used to form a portion of penetrator assembly 240. Various types of stylets and/or trocars may be disposed within an outer penetrator.

For some applications penetrator assembly 240 may include connector 250 with inner penetrator or trocar 260 extending therefrom and hub 270 with outer penetrator or cannula 280 extending therefrom. Connector 250 and hub 270 may be releasably engaged with each other using Luer type fittings, threaded connections or other suitable fittings formed on second end 252 of connector 250 and first end 271 of hub 270. Outer penetrator 280 may extend from second end 272 of hub 270.

For some applications outer penetrator or cannula 280 may be described as a generally elongated tube sized to receive inner penetrator or stylet 260 therein. Portions of inner penetrator 260 may be disposed within a longitudinal passageway 276 extending through outer penetrator 280. The outside diameter of inner penetrator 260 and the inside diameter of longitudinal passageway 276 may be selected so that inner penetrator 260 may be slidably disposed within outer penetrator 280. Outer penetrator 280 may be formed from stainless steel, titanium or other materials of suitable strength and durability to penetrate bone and magnetic characteristics to allow releasable engagement with disc 254.

Tip 281 of outer penetrator 280 and/or tip 261 of inner penetrator 260 may be operable to penetrate bone and associated bone marrow. The configuration of tips 261 and/or 281 may be selected to penetrate a bone or other body cavities with minimal trauma. First end or tip 261 of inner penetrator 260 may be trapezoid shaped and may include one or more cutting surfaces. In one embodiment outer penetrator 280 and inner penetrator 260 may be ground together as one unit during an associated manufacturing process. Inner penetrator 260 may also include a longitudinal groove (not expressly shown) that runs along the side of inner penetrator 260 to allow bone chips and/or tissues to exit an insertion site as penetrator assembly 240 is drilled deeper into an associated bone.

Hub 270 may be used to stabilize penetrator assembly 240 during insertion of outer penetrator 280 into a patient's skin, soft tissue and adjacent bone at a selected insertion site. First end 271 of hub 270 may be operable for releasable engagement or attachment with associated connector 250. Second end 272 of hub 270 may have a size and configuration compatible with an associated insertion site. The combination of hub 270 with outer penetrator 280 may sometimes be referred to as a penetrator set or an intraosseous needle.

For some applications connector 250 may be described as a generally cylindrical tube defined in part by first end 251 and second end 252. The exterior of connector 250 may include an enlarged tapered portion adjacent to end 251. A plurality of longitudinal ridges 256 may be formed on the exterior of connector 250 to allow an operator to grasp associated penetrator assembly 240 during attachment with drive shaft 216. Longitudinal ridges 256 also allow connector 250 to be grasped for disengagement from hub 270 after outer penetrator 280 has been inserted into a bone and associated bone marrow. Disc 254 may be disposed within receptacle or opening 256 for use in releasably attaching connector 250 with drive shaft 216.

For some applications disc 254 may be a magnet. For such applications drive shaft 216 may be formed from various types of metallic materials with magnetic characteristics compatible with releasable engagement of drive shaft 216 with the magnetic disc 254 disposed in penetrator assembly 240. For other applications a magnet (not expressly shown) may be formed on the end of drive shaft 216. For such applications disc 254 may be formed from various types of metallic material with characteristics compatible with releasably engaging penetrator assembly 240 with the magnet formed on the end of drive shaft 216.

First end 271 may have a generally cylindrical pin type configuration compatible with releasably engaging hub 270 with second end or box end 252 of connector 250. Second end 252 of connector 250 may include opening 258 sized to receive first end 271 of hub 270 therein. Threads 259 may be formed in opening 258 adjacent to second end 252 of connector 250. Threads 273 may be formed proximate end 271 of hub 270. Threads 259 and 273 may be used to releasably attach connector 250 with first end 271 of hub 270.

For some applications end 272 of hub 270 may have the general configuration of flange. Angular slot or groove 274 sized to receive one end of protective cover or needle cap 290 may be formed in end 272. Slot or groove 274 may be used to releasable engage cover 290 with penetrator assembly 240. For some applications cover 290 may be described as a generally hollow tube having rounded end 292. Cover 290 may be disposed within associated slot 274 to protect portions of outer penetrator 280 and inner penetrator 260 prior to attachment with a driver. Cover 290 may include a plurality of longitudinal ridges 294 formed on the exterior thereof. Longitudinal ridges 294 cooperate with each other to allow installing and removing cover or needle cap 290 without contaminating portions of an associated penetrator. Cover 290 may be formed from various plastics and/or metals.

FIG. 18B shows container 230 with penetrator assembly 240 disposed therein. One of the benefits of the present disclosure includes providing a kit which allows an operator to remove a driver from a holder contained within the kit using one hand. The other hand of the operator may remove container 230 from page two of divider 50 and open lid 232 of container 230 using one hand. Drive shaft 216 may be releasably engaged with receptacle 258 in end 251 of connector 250.

FIG. 19 shows another example of a manual driver which may be used to insert an IO device into bone marrow in accordance with teachings of the present disclosure. Manual driver 200b may include pistol grip type handle 212b with drive shaft 216 extending therefrom. Manual driver 200b may also include an optional ratchet mechanism (not expressly shown). Manual driver 200b may be releasably engaged with penetrator assembly 240 or any other IO device incorporating teachings of the present disclosure.

Examples of acute and chronic conditions which may be treated using kits, intraosseous devices, intravenous devices and procedures incorporating teachings of the present disclosure include, but are not limited to, the following:

Anaphylaxis (epinephrine, steroids, antihistamines, fluids, and life support)

Arrhythmia (anti-arrhythmics, electrolyte balance, life support);

Burns (fluid replacement, antibiotics, morphine for pain control);

Cardiac arrest (epinephrine, atropine, amiodarone, calcium, xylocalne, magnesium);

Congestive heart failure (life support, diuretics, morphine, nitroglycerin);

Dehydration (emergency port for life support, antibiotics, blood, electrolytes);

Diabetic Ketoacidosis (life support, electrolyte control, fluid replacement);

Dialysis (emergency port for life support, antibiotics, blood, electrolytes);

Drug overdose (naloxone, life support, electrolyte correction);

Emphysema (life support, beta adrenergics, steroids);

Hemophiliacs (life support, blood, fibrin products, analgesics);

Osteomyelitis (antibiotics directly into the site of infection, analgesics);

Pediatric applications (shock, dehydration, nutrition, electrolyte correction);

Seizures (anti-seizure medications, life support, fluid balance);

Shock (life support fluids, pressor agents, antibiotics, steroids);

Sickle cell crisis (fluid, morphine for pain, blood, antibiotics);

Trauma (emergency port for life support fluids, antibiotics, blood, electrolytes);

More than 35,000 Advanced Cardiac Life Support (ACLS) ambulances are in service in the U.S. Each is equipped with emergency drugs and devices. Most are required to carry intraosseous needles and paramedics are trained in their use for pediatric emergencies. Kits incorporating teachings of the present disclosure may be used to administer medications and treats before permanent damage to a patient occurs.

More than 4,000 emergency rooms in the U.S. are required to treat life-threatening emergencies like shock trauma and cardiac arrest. ERs are stocked with the latest devices and equipment to help patients receive state-of-the-art treatment. However, there is no more exasperating situation for the physician or potentially catastrophic condition for the critical patient, than the inability to establish intravenous access. Kits with IO devices incorporating teachings of the present disclosure may provide a simple and straightforward solution for extremely difficult clinical problems.

Hospitals are required to provide crash carts on every patient ward. It is estimated that 6,000 U.S. hospitals stock more than 60,000 crash carts. These crash carts are stocked with defibrillators, IV access devices, including central venous catheters, IV fluids and drugs for common emergencies. Nurses and other healthcare workers using these crash carts are often inexperienced in such emergencies and have difficulty establishing IV access. A kit with IO devices incorporating teachings of the present disclosure may provide the long sought IV alternative for difficult patients.

Automatic injectors are widely used in the military. During Desert Storm, combat soldiers carried an atropine auto-injector for nerve gas poisoning. Current auto-injectors are limited to intramuscular injections. The Kits with IO devices may vastly expand the scope of treatment to include intravenous drugs, without having to be skilled in the technique of intravenous insertion.

Most acute care hospitals in the U.S. operate Intensive Care Units (ICUs) for seriously ill patients. Establishing and maintaining venous access in these patients is often a challenge. IO access may be a welcome procedure for administration of drugs and fluids to these critical patients.

Ten percent of the population experience a major seizure in their lifetime and more than 2,500,000 people in the United States have epilepsy. Grand mal seizures represent one of the most dramatic events in medicine. During the seizure, which usually lasts 60 to 90 seconds, patients typically fall to the ground, become rigid with trunk and extremities extended, and shake violently. The most dreaded progression of seizures is status epilepticus, a condition defined as a continuous seizure lasting more than 30 minutes or two or more seizures that occur without full conscious recovery between attacks. Convulsive status epilepticus requires urgent, immediate treatment. Patients are at risk for serious injury, hypoxemia, circulatory collapse, permanent brain damage and death. The overall mortality of convulsive status epilepticus is up to 35 percent.

Intravenous access with a large bore needle/catheter must be established to administer anticonvulsant medications. These include a benzodiazepine followed by phenytoin and/or phenobarbitol for immediate seizure control and prevention of further seizures. There are no satisfactory oral, rectal, or intramuscular medications that will control status epilepticus.

The problem facing clinicians and paramedics treating patients with status epilepticus is the difficulty establishing venous access. Without adequate venous lines none of the effective anticonvulsants can be given. During seizures the violent shaking makes accessing a satisfactory vein difficult. Often after the line is established, further shaking dislodges the IV or causes it to infiltrate.

Further, caregivers are at great risk of puncturing themselves with a needle when attempting to establish venous access in a patient during a seizure. Through no fault of their own, seizing patients, by jerking and thrashing around, turn the safest procedure into a terrifying venture. Doctors, nurses, and paramedics work in mortal fear of contracting AIDS and hepatitis through an inadvertent puncture with a contaminated needle.

In an attempt to solve the venous access problem, emergency physicians and intensivists have turned to establishing a central line (intravenous catheter placed in a large central vein such as the subclavian or femoral vein). However, with this method, even under ideal conditions, there is an increased incidence of serious side effects such as pneumothorax, hemothorax, inadvertent puncture of a major artery, infection, venous thrombosis, and embolus. In the case of a patient with status epilepticus, this method becomes increasingly difficult and dangerous for all of the above-mentioned reasons. Therefore, most doctors are reluctant to even attempt a central line until seizures have ceased.

Dialysis patients who often come to the emergency room in life threatening situations such as pulmonary edema (water on the lungs) or high potassium leading to cardiac arrest. These patients typically have troublesome or non-existent veins. The IO access may give these patients hope for a better quality of live and decrease their mortality.

Drug overdose victims, often comatose, generally require immediate IV access to give antidotes and life saving medications such as Narcan. These patients usually have difficult venous access due to long term abuse of their veins. IO access may give these patients an alternate route for delivery of medications and fluids while improving the safety of the healthcare workers.

Trauma victims and attempted suicide patients, often in shock due to blood loss, may also require swift replacement of fluids to save vital organs. Because of the shock condition (decreased blood pressure), veins collapse and are often impossible to find. IO access may save precious minutes for paramedics and trauma surgeons responsible for their care.

Although the present disclosure and its advantages have been described in detail, it should be understood that various changes, substitutions and alternations can be made herein without departing from the spirit and scope of the invention as defined by the following claims.

What is claimed is:

1. A vascular access kit comprising:
components for accessing a peripheral vein;
components for accessing bone marrow at a selected intraosseous site, the components for accessing bone marrow comprising:
a penetrator; and
a powered driver having a body and a handle, and configured to insert the penetrator along an axis extending through the body, the handle extending from the body at a non-parallel angle to the axis; and
a cradle configured to secure and releasably engage the powered driver in a downward orientation such that the axis extends through a plane of a base of the cradle, the cradle further comprising a rigid trigger guard configured to obstruct access to an exterior surface of a trigger of the powered driver to prevent accidental activation of the powered driver.

2. The kit of claim 1 wherein the penetrator comprises an intraosseous needle set.

3. The kit of claim 1 wherein the kit further comprises at least one divider operable to releasably hold in an organized sequence an intravenous access device and an intraosseous access device.

4. A kit for accessing the vascular system of a patient comprising:
an intravenous (IV) access device and an intraosseous (IO) access device comprising:
a penetrator; and
a powered driver having a body and a handle, and configured to insert the penetrator along an axis extending through the body, the handle extending from the body at a non-parallel angle to the axis;
a securing device attached to an interior surface of the kit; and
the securing device sized to releasably engage the powered driver,
wherein the securing device comprises a cradle configured to secure and releasably engage the powered driver, the cradle further comprising a rigid trigger guard including walls configured to obstruct access to opposing lateral surfaces of a trigger of the powered driver to prevent accidental activation of the powered driver.

5. A kit according to claim 4, further comprising:
a divider disposed in the kit with the penetrator releasably engaged with one surface of the divider; and
the penetrator operable to be releasably engaged with the powered driver.

6. A kit according to claim 5, wherein the securing device is configured to allow a user to easily replace the powered driver into the kit for subsequent use.

7. A kit for accessing the vascular system of a patient comprising:
an intravenous (IV) access device and an intraosseous (IO) access device comprising:
a penetrator; and
a powered driver having a body and a handle, and configured to insert the penetrator along an axis extending through the body, the handle extending from the body at a non-parallel angle to the axis; and
a cradle attached to an interior surface of the kit and sized to releasably engage the powered driver in a downward orientation such that the axis extends through a plane of a base of the cradle, the driver used to provide intraosseous access to the vascular system of a patient.

8. A kit according to claim 7, wherein the cradle is configured to allow a user to easily pick up the powered driver, the kit further comprising:
a divider disposed in the kit and the penetrator releasably engaged with one surface of the divider; and
the penetrator operable to be releasably engaged with the powered driver.

9. A vascular access kit for accessing a patient's vascular system comprising:
a driver and a penetrator assembly;
the driver having a body and a handle, and operable to insert a portion of the penetrator assembly into bone marrow of a patient along an axis extending through the body, the handle extending from the body at a non-parallel angle to the axis;
unit doses of medications for delivery to the bone marrow through the portion of the penetrator assembly; and
a cradle attached to an interior surface of the kit and sized to releasably engage the driver in a downward orientation such that the axis extends through a plane of a base of the cradle, the cradle further comprising a rigid trigger guard configured to obstruct access to an exterior surface of a trigger of the powered driver to prevent accidental activation of the powered driver.

10. The kit of claim 9 wherein the medications comprise epinephrine, atropine, diazepam, amiodarane, and narcan.

11. A kit according to claim 7, wherein the driver comprises a powered driver.

12. A kit according to claim 7, wherein the driver comprises a manual driver.

13. A kit according to claim 9, where in the driver comprises a powered driver.

14. The kit according to claim 9, wherein the driver comprises a manual driver.

\* \* \* \* \*

UNITED STATES PATENT AND TRADEMARK OFFICE
CERTIFICATE OF CORRECTION

| | | |
|---|---|---|
| PATENT NO. | : 9,072,543 B2 | Page 1 of 1 |
| APPLICATION NO. | : 11/380340 | |
| DATED | : July 7, 2015 | |
| INVENTOR(S) | : Miller et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1618 days.

Signed and Sealed this
Twenty-sixth Day of January, 2016

Michelle K. Lee
*Director of the United States Patent and Trademark Office*